US009175407B2

(12) United States Patent
Kaczur et al.

(10) Patent No.: US 9,175,407 B2
(45) Date of Patent: Nov. 3, 2015

(54) INTEGRATED PROCESS FOR PRODUCING CARBOXYLIC ACIDS FROM CARBON DIOXIDE

(71) Applicant: Liquid Light, Inc., Monmouth Junction, NJ (US)

(72) Inventors: Jerry J. Kaczur, North Miami Beach, FL (US); Kyle Teamey, Washington, DC (US)

(73) Assignee: Liquid Light, Inc., Monmouth Junction, NJ (US)

( * ) Notice: Subject to any disclaimer, the term of this patent is extended or adjusted under 35 U.S.C. 154(b) by 0 days.

(21) Appl. No.: 13/724,339

(22) Filed: Dec. 21, 2012

(65) Prior Publication Data

US 2013/0175181 A1 Jul. 11, 2013

Related U.S. Application Data

(60) Provisional application No. 61/715,060, filed on Oct. 17, 2012, provisional application No. 61/720,670, filed on Oct. 31, 2012, provisional application No. 61/675,938, filed on Jul. 26, 2012, provisional (Continued)

(51) Int. Cl.

*C25B 3/04* (2006.01)
*C25B 1/22* (2006.01)
*C07C 51/02* (2006.01)

(Continued)

(52) U.S. Cl.

CPC . *C25B 1/22* (2013.01); *C07C 51/02* (2013.01); *C07C 51/10* (2013.01); *C07C 51/41* (2013.01); *C25B 3/02* (2013.01); *C25B 3/04* (2013.01); *C25B 3/06* (2013.01); *C25B 9/08* (2013.01)

(58) Field of Classification Search

None

See application file for complete search history.

(56) References Cited

U.S. PATENT DOCUMENTS 659,733 A 10/1900 Goldschmidt
820,159 A 5/1906 Weise et al.

(Continued)

FOREIGN PATENT DOCUMENTS

CA 1146120 A1 5/1983
CA 1272161 A1 7/1990

(Continued)

OTHER PUBLICATIONS

Fischer, "Liquid Fuels from Water Gas", Industrial and Engineering Chemistry, vol. 17, No. 6, Jun. 1925, pp. 574-576.*

(Continued)

*Primary Examiner* — Harry D Wilkins, III
(74) *Attorney, Agent, or Firm* — Suiter Swantz pc llo

(57) ABSTRACT

The present disclosure is a method and system for production of carboxylic based chemicals, including carboxylic acids and salts. A method for producing at oxalic acid may include receiving an anolyte feed at an anolyte region of an electrochemical cell including an anode and receiving a catholyte feed including carbon dioxide and an alkali metal hydroxide at a catholyte region of the electrochemical cell including a cathode. Method may include applying an electrical potential between the anode and cathode sufficient to reduce the carbon dioxide to at least one reduction product and converting the at least one reduction product and the alkali metal hydroxide to an alkali metal oxalate via a thermal reactor. The method may further include receiving the alkali metal oxalate at an electrochemical acidification electrolyzer and converting the alkali metal oxalate to oxalic acid at the electrochemical acidification electrolyzer.

13 Claims, 8 Drawing Sheets

Acetate / Acetic Acid (or other chemicals)

Bromoethane (or other halogenated alkane)

$H^+$

HBr (or HX)

$H_2O$

Ethanol (or other alcohol or glycol)

$CO_2$

HBr (or HX)

Ethane (or other alkane)

Related U.S. Application Data application No. 61/703,158, filed on Sep. 19, 2012, provisional application No. 61/703,229, filed on Sep. 19, 2012, provisional application No. 61/703,175, filed on Sep. 19, 2012, provisional application No. 61/703,231, filed on Sep. 19, 2012, provisional application No. 61/703,232, filed on Sep. 19, 2012, provisional application No. 61/703,234, filed on Sep. 19, 2012, provisional application No. 61/703,238, filed on Sep. 19, 2012, provisional application No. 61/703,187, filed on Sep. 19, 2012.

(51) Int. Cl.

| | |
|---|---|
| ***C25B 3/02*** | (2006.01) |
| ***C25B 9/08*** | (2006.01) |
| ***C25B 3/06*** | (2006.01) |
| ***C07C 51/10*** | (2006.01) |
| ***C07C 51/41*** | (2006.01) |

(56) References Cited

U.S. PATENT DOCUMENTS 1,017,261 A 2/1912 Hempel
1,038,985 A 9/1912 Strauss
1,280,622 A * 10/1918 Andrews ........................ 562/597
1,349,947 A 8/1920 Dupont et al.
1,420,213 A 6/1922 Paulus
1,445,163 A 2/1923 Paulus
1,506,872 A 9/1924 Wallace
1,602,802 A 10/1926 Wallace
1,962,140 A 6/1934 Dreyfus
2,033,097 A 3/1936 Enderli et al.
2,281,715 A 5/1942 Rogers
3,019,256 A 1/1962 Dunn
3,088,990 A 5/1963 Rightmire et al.
3,236,879 A 2/1966 Chiusoli
3,293,292 A 12/1966 Olivier et al.
3,326,998 A 6/1967 Reusser et al.
3,341,615 A 9/1967 Wulf et al.
3,341,616 A 9/1967 Vives
3,344,046 A 9/1967 Neikam
3,347,758 A 10/1967 Koehl, Jr.
3,352,935 A 11/1967 Mahan
3,361,653 A 1/1968 Miller
3,401,100 A 9/1968 Macklin
3,492,209 A 1/1970 Miller
3,531,386 A 9/1970 Heredy
3,560,354 A 2/1971 Young
3,607,962 A 9/1971 Krekeler et al.
3,636,159 A 1/1972 Solomon
3,646,131 A 2/1972 Ikarasi et al.
3,720,591 A 3/1973 Skarlos
3,745,180 A 7/1973 Rennie
3,764,492 A 10/1973 Baizer et al.
3,779,875 A 12/1973 Michelet
3,824,163 A 7/1974 Maget
3,894,059 A 7/1975 Selvaratnam
3,928,435 A 12/1975 Awane et al.
3,959,094 A * 5/1976 Steinberg ...................... 205/450
4,072,583 A 2/1978 Hallcher et al.
4,087,470 A 5/1978 Suzuki
4,088,682 A 5/1978 Jordan
4,145,405 A 3/1979 Gorin
4,147,599 A 4/1979 O'Leary et al.
4,162,948 A 7/1979 Yagii et al.
4,219,392 A 8/1980 Halmann
4,245,114 A 1/1981 Peltzman
4,253,921 A 3/1981 Baldwin et al.
4,256,550 A 3/1981 Niinobe et al.
4,267,070 A 5/1981 Nefedov et al.
4,299,981 A 11/1981 Leonard
4,343,690 A 8/1982 De Nora
4,381,978 A 5/1983 Gratzel et al.
4,421,613 A 12/1983 Goodridge et al.
4,450,055 A 5/1984 Stafford
4,476,003 A 10/1984 Frank et al.
4,510,214 A 4/1985 Crouse et al.
4,523,981 A 6/1985 Ang et al.
4,545,886 A 10/1985 De Nora et al.
4,547,271 A 10/1985 Bharucha et al.
4,560,451 A 12/1985 Nielsen
4,563,254 A 1/1986 Morduchowitz et al.
4,589,963 A * 5/1986 Cipriano et al. .............. 205/435
4,595,465 A 6/1986 Ang et al.
4,608,132 A 8/1986 Sammells
4,608,133 A 8/1986 Morduchowitz et al.
4,619,743 A 10/1986 Cook
4,661,422 A 4/1987 Marianowski et al.
4,673,473 A 6/1987 Ang et al.
4,702,973 A 10/1987 Marianowski
4,732,655 A 3/1988 Morduchowitz et al.
4,756,807 A * 7/1988 Meyer et al. ................. 205/555
4,810,596 A 3/1989 Ludwig
4,845,252 A 7/1989 Schmidt et al.
4,902,828 A 2/1990 Wickenhaeuser et al.
4,950,368 A 8/1990 Weinberg et al.
4,968,393 A 11/1990 Mazur et al.
5,074,974 A 12/1991 Toomey, Jr.
5,084,148 A * 1/1992 Kazcur et al. ................ 205/503
5,106,465 A 4/1992 Kaczur et al.
5,107,040 A 4/1992 Repman et al.
5,155,256 A 10/1992 Chapman
5,198,086 A 3/1993 Chlanda et al.
5,246,551 A 9/1993 Pletcher et al.
5,290,404 A 3/1994 Toomey et al.
5,294,319 A 3/1994 Kaczur et al.
5,300,369 A 4/1994 Dietrich et al.
5,412,150 A 5/1995 Wessel
5,443,804 A 8/1995 Parker et al.
5,455,372 A 10/1995 Hirai et al.
5,474,658 A 12/1995 Scharbert et al.
5,514,492 A 5/1996 Marincic et al.
5,536,856 A 7/1996 Harrison et al.
5,654,493 A 8/1997 Wessel
5,804,045 A 9/1998 Orillon et al.
5,961,813 A 10/1999 Gestermann et al.
6,001,500 A 12/1999 Bass et al.
6,024,935 A 2/2000 Mills et al.
6,137,005 A 10/2000 Honevik
6,171,551 B1 1/2001 Malchesky et al.
6,251,256 B1 6/2001 Blay et al.
6,312,655 B1 11/2001 Hesse et al.
6,348,613 B2 2/2002 Miyamoto et al.
6,380,446 B1 4/2002 Drew et al.
6,465,699 B1 10/2002 Grosso
6,492,047 B1 12/2002 Peled et al.
6,777,571 B2 8/2004 Chaturvedi et al.
6,881,320 B1 4/2005 Krafton et al.
6,949,178 B2 9/2005 Tennakoon et al.
7,138,201 B2 11/2006 Inoue et al.
7,462,752 B2 12/2008 Fong et al.
7,883,610 B2 2/2011 Monzyk et al.
8,227,127 B2 7/2012 Little et al.
8,277,631 B2 10/2012 Eastman et al.
8,313,634 B2 11/2012 Bocarsly et al.
8,444,844 B1 5/2013 Teamey et al.
8,562,811 B2 10/2013 Sivasankar et al.
8,663,447 B2 3/2014 Bocarsly et al.
2001/0001798 A1 5/2001 Sharpless et al.
2001/0026884 A1 10/2001 Appleby et al.
2002/0013477 A1 1/2002 Kim et al.
2002/0022753 A1 2/2002 Drew et al.
2002/0122980 A1 9/2002 Fleischer et al.
2004/0115489 A1 6/2004 Goel
2005/0139486 A1 6/2005 Carson et al.
2005/0245784 A1 11/2005 Carson et al.
2006/0102468 A1 5/2006 Monzyk et al.
2006/0269813 A1 11/2006 Seabaugh et al.
2007/0004023 A1 1/2007 Trachtenberg et al.
2007/0012577 A1 1/2007 Bulan et al.
2007/0224479 A1 9/2007 Tadokoro et al.
2008/0223727 A1 9/2008 Oloman et al.

(56) References Cited

U.S. PATENT DOCUMENTS

| | | | |
|---|---|---|---|
| 2008/0245660 | A1 | 10/2008 | Little et al. |
| 2008/0248350 | A1 | 10/2008 | Little et al. |
| 2008/0283411 | A1 | 11/2008 | Eastman et al. |
| 2008/0286643 | A1 | 11/2008 | Iwasaki |
| 2008/0296146 | A1 | 12/2008 | Toulhoat et al. |
| 2008/0314758 | A1 | 12/2008 | Grosso et al. |
| 2009/0000956 | A1 | 1/2009 | Weidner et al. |
| 2009/0014336 | A1 | 1/2009 | Olah et al. |
| 2009/0030240 | A1 | 1/2009 | Olah et al. |
| 2009/0057161 | A1 | 3/2009 | Aulich et al. |
| 2009/0062110 | A1 | 3/2009 | Koshino et al. |
| 2009/0156867 | A1 | 6/2009 | Van Kruchten |
| 2009/0308759 | A1 | 12/2009 | Waycuilis |
| 2010/0051859 | A1 | 3/2010 | House et al. |
| 2010/0061922 | A1 | 3/2010 | Rauser et al. |
| 2010/0069600 | A1 | 3/2010 | Morelle et al. |
| 2010/0130768 | A1 | 5/2010 | Sato et al. |
| 2010/0140103 | A1 | 6/2010 | Gilliam et al. |
| 2010/0187123 | A1 | 7/2010 | Bocarsly et al. |
| 2010/0187125 | A1 | 7/2010 | Sandoval et al. |
| 2010/0191024 | A1 | 7/2010 | Uenveren et al. |
| 2010/0196800 | A1 | 8/2010 | Markoski et al. |
| 2010/0248042 | A1 | 9/2010 | Nakagawa et al. |
| 2010/0270167 | A1 | 10/2010 | McFarland |
| 2010/0282614 | A1 | 11/2010 | Detournay et al. |
| 2010/0305629 | A1 | 12/2010 | Lund et al. |
| 2010/0330435 | A1 | 12/2010 | Nemeth et al. |
| 2011/0024288 | A1 | 2/2011 | Bhavaraju et al. |
| 2011/0083968 | A1 | 4/2011 | Gilliam et al. |
| 2011/0114501 | A1 | 5/2011 | Teamey et al. |
| 2011/0114502 | A1 | 5/2011 | Cole et al. |
| 2011/0114503 | A1 | 5/2011 | Sivasankar et al. |
| 2011/0114504 | A1 | 5/2011 | Sivasankar et al. |
| 2011/0143929 | A1 | 6/2011 | Sato et al. |
| 2011/0177398 | A1 | 7/2011 | Affinito et al. |
| 2011/0186441 | A1 | 8/2011 | LaFrancois et al. |
| 2011/0217226 | A1 | 9/2011 | Mosa et al. |
| 2011/0226632 | A1 | 9/2011 | Cole et al. |
| 2011/0237830 | A1 | 9/2011 | Masel |
| 2011/0303551 | A1 | 12/2011 | Gilliam et al. |
| 2011/0318617 | A1 | 12/2011 | Kirchev et al. |
| 2012/0004448 | A1 | 1/2012 | Bhattacharyya et al. |
| 2012/0004449 | A1 | 1/2012 | Bhattacharyya |
| 2012/0004454 | A1 | 1/2012 | Bhattacharyya et al. |
| 2012/0018311 | A1 | 1/2012 | Yotsuhashi et al. |
| 2012/0043301 | A1 | 2/2012 | Arvin et al. |
| 2012/0132537 | A1 | 5/2012 | Sivasankar et al. |
| 2012/0132538 | A1 | 5/2012 | Cole et al. |
| 2012/0199493 | A1 | 8/2012 | Krafft et al. |
| 2012/0215034 | A1 | 8/2012 | McFarland |
| 2012/0228147 | A1 | 9/2012 | Sivasankar et al. |
| 2012/0277465 | A1 | 11/2012 | Cole et al. |
| 2012/0292196 | A1 | 11/2012 | Albrecht et al. |
| 2012/0295172 | A1 | 11/2012 | Peled et al. |
| 2012/0298522 | A1 | 11/2012 | Shipchandler et al. |
| 2012/0329657 | A1 | 12/2012 | Eastman et al. |
| 2013/0062216 | A1 | 3/2013 | Yotsuhashi et al. |
| 2013/0098772 | A1 | 4/2013 | Bocarsly et al. |
| 2013/0105304 | A1 | 5/2013 | Kaczur et al. |
| 2013/0105330 | A1 | 5/2013 | Teamey et al. |
| 2013/0118907 | A1 | 5/2013 | Deguchi et al. |
| 2013/0118911 | A1 | 5/2013 | Sivasankar et al. |
| 2013/0134048 | A1 | 5/2013 | Teamey et al. |
| 2013/0134049 | A1 | 5/2013 | Teamey et al. |
| 2013/0137898 | A1 | 5/2013 | Teamey et al. |
| 2013/0140187 | A1 | 6/2013 | Teamey et al. |
| 2013/0180863 | A1 | 7/2013 | Kaczur et al. |
| 2013/0180865 | A1 | 7/2013 | Cole et al. |
| 2013/0186771 | A1 | 7/2013 | Zhai et al. |
| 2013/0199937 | A1 | 8/2013 | Cole et al. |

FOREIGN PATENT DOCUMENTS

| | | | |
|---|---|---|---|
| CA | 2043256 | A1 | 12/1991 |
| CA | 2391938 | A1 | 5/2001 |
| CN | 85103377 | A | 10/1986 |
| CN | 87102067 | A | 4/1988 |
| CN | 1047381 | C | 12/1999 |
| CN | 1502599 | A | 6/2004 |
| CN | 1244534 | C | 3/2006 |
| CN | 1903821 | B | 1/2007 |
| CN | 1319927 | C | 6/2007 |
| CN | 100999462 | A | 7/2007 |
| CN | 101743343 | A | 6/2010 |
| CN | 101462943 | B | 6/2011 |
| CN | 102190573 | A | 9/2011 |
| CN | 101077855 | B | 12/2011 |
| CN | 102391099 | A | 3/2012 |
| CN | 1927805 | B | 5/2012 |
| DE | 1047765 | A | 12/1958 |
| DE | 2301032 | A | 7/1974 |
| EP | 0028430 | A1 | 5/1981 |
| EP | 2329875 | A1 | 6/2011 |
| FR | 853643 | | 3/1940 |
| GB | 1096847 | A | 12/1967 |
| GB | 1223452 | A | 2/1971 |
| GB | 1285209 | A | 8/1972 |
| GB | 1584524 | A | 4/1977 |
| GB | 2038335 | A | 7/1980 |
| GB | 2312218 | A | 10/1997 |
| JP | 64-015388 | | 1/1989 |
| WO | 91/01947 | A1 | 2/1991 |
| WO | WO 9724320 | A1 | 7/1997 |
| WO | 9850974 | A1 | 11/1998 |
| WO | WO 0015586 | A1 | 3/2000 |
| WO | WO0138275 | A1 | 5/2001 |
| WO | WO 2004067673 | A1 | 8/2004 |
| WO | 2006074335 | A2 | 7/2006 |
| WO | 2007041872 | A1 | 4/2007 |
| WO | WO 2007041872 | A1 | 4/2007 |
| WO | 2007/091616 | A1 | 8/2007 |
| WO | 2009108327 | A1 | 9/2009 |
| WO | 2011069008 | | 6/2011 |
| WO | 2011116236 | A2 | 9/2011 |
| WO | 2011160577 | A1 | 12/2011 |
| WO | 2012015921 | A1 | 2/2012 |
| WO | WO 2012046362 | A1 | 4/2012 |
| WO | 2012166997 | A2 | 12/2012 |

OTHER PUBLICATIONS

Williamson et al, "Rate of Absorption and Equilibrium of Carbon Dioxde in Alkaline Solutions", Industrial and Engineering Chemistry, vol. 16, No. 11, Nov. 1924, pp. 1157-1161.*

Hori, "Electrochemical CO2 Reduction on Metal Electrodes", Modern Aspects of Electrochemistry, No. 42, 2008, pp. 89-189.*

Seshardi G., Lin C., Bocarsly A.B., A new homogeneous electrocatalyst for the reduction of carbon dioxide to methanol at low overpotential, Journal of Electroanalytical Chemistry, 1994, 372, pp. 145-150.

Seshadri et al., "A new homogeneous electrocatalyst for the reduction of carbon dioxide to methanol at low overpotential", Journal of Electroanalytical Chemistry and Interfacial Electro Chemistry, Elsevier, Amsterdam, NL, vol. 372, No. 1-2, Jul. 8, 1994, pp. 145-150.

Hossain et al., "Palladium and cobalt complexes of substituted quinoline, bipyridine and phenanthroline as catalysts for electrochemical reduction of carbon dioxide", Electrochimica Acta, Elsevier Science Publishers, vol. 42, No. 16, Jan. 1, 1997, pp. 2577-2585.

Fisher et al., "Electrocatalytic reduction of carbon dioxide by using macrocycles of nickel and cobalt", Journal of the American Chemical Society, vol. 102, No. 24, Sep. 1, 1980, pp. 7361-7363.

Ishida et al., Selective Formation of HC00—in the Electrochemical CO2 Reduction Catalyzed by URU(BPY)2(CO)2 3/4 2+ (BPY = 2,2'-Bipyridine), Journal of the Chemical Society, Chemical Communications, Chemical Society, Letchworth, GB, Jan. 1, 1987, pp. 131-132.

(56) References Cited

OTHER PUBLICATIONS

Zhao et al., "Electrochemical reduction of supercritical carbon dioxide in ionic liquid 1-n-butyl-3-methylimidazolium hexafluorophosphate", Journal of Supercritical Fluids, PRA Press, US, vol. 32, No. 1-3, Dec. 1, 2004, pp. 287-291.
Hori et al, chapter on "Electrochemical CO2 Reduction on Metal Electrodes," in the book "Modern Aspects of Electrochemistry," vol. 42, pp. 106 and 107.
Czerwinski et al, "Adsorption Study of CO2 on Reticulated vitreous carbon (RVC) covered with platinum," Analytical Letters, vol. 18, Issue 14 (1985), pp. 1717-1722.
Hammouche et al, Chemical Catalysis of Electrochemical Reactions. Homogeneous Catalysis of the Electrochemical Reduction of Carbon Dioxide by Iron ("0") Porphyrins. Role of the Addition of Magnesium Cations. J. Am. Chem. Soc. 1991, 113, 8455-8466.
Hossain et al., Palladium and Cobalt Complexes of Substituted Quinoline, Bipyridine and Phenanthroline as Catalysts for Electrochemical Reduction of Carbon Dioxide, Electrochimica Acta (no month, 1997), vol. 42, No. 16, pp. 2577-2785.
Scibioh et al., "Electrochemical Reduction of Carbon Dioxide: A Status Report", Proc Indian Natn Sci Acad (May 2004), vol. 70, A, No. 3, pp. 407-462.
T. Meisel, Z. Halmos, K Seybold, and E. Pungor, The Thermal Decomposition of Alkali Metal Formates, Journal of Thermal Analysis, vol. 7 (1975) 73-80.
Eggins, Brown, McNeill, and Grimshaw, Carbon Dioxide Fixation by Electrochemical Reduction in Water to Oxalate and Glyoxylate, Tetrahedron Letters vol. 29, No. 8, pp. 945-948, 1988, Pergamon Journals Ltd., Printed in Great Britain.
M. Alvarez-Guerra et al., Conversion of carbon dioxide into formate using a continuous electrochemical reduction process in a lead cathode, Chem. Eng. J. (2012), http://dx.doi.org/10.1016/j.cej.2012.06.099.
Afroza Begum, Electrochemical CO2 Reduction, Thesis, 2011, University of Newfoundland, http://collections.mun.ca/cdm4/document.php?CISOROOT=/theses5&CISOPTR=14718&REC=7.
Satoshi Kaneco, Kenji Iiba, Nobu-Hide Hiei, Kiyohisa Ohta, Takayuki Mizuno, and Tohru Suzuki, Electrochemical reduction of carbon dioxide to ethylene with high Faradaic efficiency at a Cu electrode in CsOH/methanol, Electrochimica Acta 44 (1999) 4701-4706.
Keith Scott, A Preliminary Investigation of the Simultaneous Anodic and Cathodic Production of Glyoxylic Acid, Electrochimica Acta, vol. 36, No. 9, pp. 1447-1452, 1991, Printed in Great Britain.
B. Eneau-Innocent et al., Electroreduction of carbon dioxide at a lead electrode in propylene carbonate: A spectroscopic study, Applied Catalysis B: Environmental 98 (2010) 65-71.
Kotaro Ogura et al., Selective Conversion of CO2 to Ethylene by the Electrolysis at a Three-Phase (Gas/Liquid/Solid) Interface in an Acidic Solution Containing Cupric Ions, Fuel Chemistry Division Preprints 2003, 48(1), 264.
S. Gambino and G. Silvestri, On the electrochemical reduction of carbon dioxide and ethylene, Tetrahedron Letters No. 32, pp. 3025-3028, 1973, Pergamon Press, Printed in Great Britain.
K.S. Udupa, G.S. Subramanian, and H.V.K. Udupa, The electrolytic reduction of carbon dioxide to formic acid, Electrochimica Acta, 1971, vol. 16, pp. 1593 to 1598, Pergamon Press, Printed in Northern Ireland.
Kiyoshi Kudo et al., Synthesis of oxalate from carbon monoxide and carbon dioxide in the presence of caesium carbonate, J. Chem. Soc., Perkin Trans. 2, 1997, pp. 679-682.
M.C. Boswell and J.V. Dickson, The Action of Sodium Hydroxide on Carbon Monoxide, Sodium Formate and Sodium Oxalate, J. Americam Chem. Soc., vol. 80, 1918, pp. 1779-1786.
Green et al., "Vapor-Liquid Equilibria of Formaldehyde-Methanol-Water", Industrial and Engineering Chemistry (Jan. 1955), vol. 47, No. 1, pp. 103-109.
Shibata et al., "Electrochemical Synthesis of Urea at Gas-Diffusion Electrodes Part VI. Simultaneous Reduction of Carbon Dioxide and Nitrite Ions with Various Metallophthalocyanine Catalysts". J. Of Electroanalytical Chemistry (no month, 2001), vol. 507, pp. 177-184.
Jaaskelainen and Haukka, The Use of Carbon Dioxide in Ruthenium Carbonyl Catalyzed 1-hexene Hydroformylation Promoted by Alkali Metal and Alkaline Earth Salts, Applied Catalysis A: General, 247, 95-100 (2003).
Heldebrant et al., "Reversible Zwitterionic Liquids, The Reaction of Alkanol Guanidines, Alkanol Amidines, and Diamines wih CO2", Green Chem. (mo month, 2010), vol. 12, pp. 713-721.
Perez et al., "Activation of Carbon Dioxide by Bicyclic Amidines", J. Org. Chem. (no month, 2004), vol. 69, pp. 8005-8011.
Seshadri et al., A New Homogeneous Electrocatalyst for the Reduction of Carbon Dioxide to Methanol at Low Overpotential, Journal of Electroanalytical Chemistry, 372 (1994), 145-50.
Green et al., Vapor-Liquid Equilibria of Formaldehyde-Methanol-Water, Industrial and Engineering Chemistry (Jan. 1955), vol. 47, No. 1, pp. 103-109.
Scibioh et al., Electrochemical Reduction of Carbon Dioxide: A Status Report, Proc Indian Natn Sci Acad (May 2004), vol. 70, A, No. 3, pp. 407-462.
Gennaro et al., Homogeneous Electron Transfer Catalysis of the Electrochemical Reduction of Carbon Dioxide. Do Aromatic Anion Radicals React in an Outer-Sphere Manner?, J. Am. Chem. Soc. (no month, 1996), vol. 118, pp. 7190-7196.
Perez et al., Activation of Carbon Dioxide by Bicyclic Amidines, J. Org. Chem. (no month, 2004), vol. 69, pp. 8005-8011.
Zaragoza Dorwald, Side Reactions in Organic Synthesis, 2005, Wiley-VCH Verlag GmbH & Co. KGaA, Weinheim, Preface. p. IX.
Liansheng et al, Journal of South Central University Technology, Electrode Selection of Electrolysis with Membrane for Sodium Tungstate Solution, 1999, 6(2), pp. 107-110.
Mahmood et al., Use of Gas-Diffusion Electrodes for High-Rate Electrochemical Reduction of Carbon Dioxide. II. Reduction at Metal Phthalocyanine-Impregnated Electrodes, J. of Appl. Electrochem. (no month, 1987), vol. 17, pp. 1223-1227.
Tanno et al., Electrolysis of Iodine Solution in a New Sodium Bicarbonate-Iodine Hybrid Cycle, International Journal of Hydrogen Energy (no month, 1984), vol. 9, No. 10, pp. 841-848.
Scibioh et al, "Electrochemical Reductin of Carbon Dioxide: A Status Report," Proc. Indian Natn Science Acad., 70, A, No. 3, May 2004, pp. 407-762.
Fukaya et al., "Electrochemical Reduction of Carbon Dioxide to Formate Catalyzed by Rh(bpy)3Cl3", Kagaku Gijutsu Kenkyusho Hokoku (no month, 1986), vol. 81, No. 5, pp. 255-258. 1-page abstract only.
Li et al., "The Electro-Reduction of Carbon Dioxide in a Continuous Reactor", J. Of Applied Electrochemistry (no month, 2005), vol. 35, pp. 955-965.
Kaneco et al., "Electrochemical Reduction of Carbon Dioxide to Ethylene with High Faradaic Efficiency at a Cu Electrode in CsOH/ Methanol", Electrochimica Acta (no month, 1999), vol. 44, pp. 4701-4706.
Yuan et al., "Electrochemical Activation of Carbon Dioxide for Synthesis of Dimethyl Carbonate in an Ionic Liquid", Electrochimica Acta (no month, 2009), vol. 54, pp. 2912-2915.
U.S. Appl. No. 13/724,647, filed Dec. 21, 2012; Office Action mailed Oct. 17, 2013.
U.S. Appl. No. 13/787,481, filed Mar. 6, 2013; Office Action mailed Sep. 13, 2013.
U.S. Appl. No. 13/724,082, filed Dec. 21, 2012; Office Action mailed Aug. 12, 2013.
U.S. Appl. No. 13/724,522, filed Dec. 21, 2012; Office Action mailed Oct. 1, 2013.
U.S. Appl. No. 13/724,885, filed Dec. 21, 2012; Office Action mailed Aug. 21, 2013.
U.S. Appl. No. 13/724,231, filed Dec. 21, 2012; Office Action mailed Aug. 20, 2013.
Kaneco et al., "Electrochemical Conversion of Carbon Dioxide to Formic Acid on Pb in KOH/Methanol Electrolyte at Ambient Temperature and Pressure", Energy (no month, 1998), vol. 23, No. 12, pp. 1107-1112.

(56) References Cited

OTHER PUBLICATIONS

Wu et al., “Electrochemical Reduction of Carbon Dioxide I. Effects of the Electrolyte on the Selectivity and Activity with Sn Electrode”, Journal of the Electrochemical Society (no month, 2012), vol. 159, No. 7, pp. F353-F359.

Chaplin et al., “Effects of Process Conditions and Electrode Material on Reaction Pathways for Carbon Dioxide Electroreduction with Particular Reference to Formate Formation”, Journal of Applied Electrochemistry (no month, 2003), vol. 33, pp. 1107-1123.

Jaime-Ferrer et al., “Three-Compartment Bipolar Membrane Electrodialysis for Splitting of Sodium Formate into Formic Acid and Sodium Hydroxide: Role of Diffusion of Molecular Acid”, Journal of Membrane Science (no month, 2008), vol. 325, pp. 528-536.

James Grimshaw, Electrochemical Reactions and Mechanisms in Organic Chemistry, 2000, ISBN 978-0-444-72007-8. [retrieved on Jan. 3, 2014]. Retrieved from the Internet. <URL: http://f3.tiera.ru/ShiZ/Great%20Science%20TextBooks/Great%Science%20Textbooks%20DVD%20Library%202007%20-%20Supplement%20Five/Chemistry/Organic%20Chemistry/Electrochemical%20Reactions%20and%20Mechanisms%20in%20Organic%20Chemistry%20-%20J.%20Grimshaw%20%28Elsevier,%202000%29%WW.pdf>.

Fischer, J. et al. “The production of oxalic acid from CO2 and H2O.” Journal of Applied Electrochemistry, 1981, vol. 11, pp. 743-750.

Goodridge, F. et al., The electrolytic reduction of carbon dioxide and monoxide for the production of carboxylic acids.: Journal of applied electrochemistry, 1984, vol. 14, pp. 791-796.

Seshadri et al, “A new homogeneous catalyst for the reduction of carbon dioxide to methanol at low overpotential,” Journal of Electroanalytical Chemistry, 372 (1994) 145-150.

Scibioh et al, “Electrochemical Reduction of Carbon Dioxide: A Status Report,” Proc. Indian Natn Science Acad., 70, A, No. 3, May 2004, pp. 407-762.

Hori et al, “Enhanced Formation of Ethylene and Alcohols at Ambient Temperature and Pressure in Electrochemical Reduction of Carbon Dioxide at a Copper Electrode,” J. Chem. Soc. Chem. Commun. (1988), pp. 17-19.

Hossain et al, “Palladium and Cobalt Complexes of Substituted Quinoline, Bipyridine and Phenanthroline as Catalysts for Electrochemical Reduction of Carbon Dioxide,” Electrochimica Acta, vol. 42, No. 16 (1997), pp. 2577-2585.

Williamson et al, “Rate of Absorption and Equilibrium of Carbon Dioxide in Alkaline Solutions”, Industrial and Engineering Chemistry, vol. 16, No. 11, Nov. 1924, pp. 1157-1161.

Chen et al., “Tin oxide dependence of the CO2 reduction efficiency on tin electrodes and enhanced activity for tin/tin oxide thin-film catalysts.” Journal of the American Chemical Society 134, No. 4 (2012): 1986-1989, Jan. 9, 2012, retrieved on-line.

Zhou et al. “Anodic passivation processes of indium in alkaline solution [J]” Journal of Chinese Society for Corrosion and Protection 1 (2005): 005, Feb. 2005.

Fukaya et al., “Electrochemical Reduction of Carbon Dioxide to Formate Catalyzed by Rh(bpy)3CI3”, Kagaku Gijutsu Kenkyusho Hokoku (no month, 1986), vol. 81, No. 5, pp. 255-258.

Tinnemans et al., “Tetraaza-macrocyclic cobalt(II) and nickel(II) complexes as electron-transfer agents in the photo (electro)chemical and electrochemical reduction of carbon dioxide,” Recl.Trav. Chim. Pays-Bas, Oct. 1984, 103: 288-295.

Bocarsly et al., “Photoelectrochemical conversion of carbon dioxide to methanol and higher alcohols, a chemical carbon sequestration strategy,” Preprints of Symposia—American Chemical Society, Division of Fuel Chemistry, Volume: 53, Issue: 1, pp. 240-241.

Nefedov and Manov-Yuvenskii, The Effect of Pyridine Bases and Transition-Metal Oxides on the Activity of PdCl2 in the Carbonylation of Aromatic Mononitro Compounds by Carbon Monoxide, 28 Bulletin of the Acad. Of Sciences of the USSR 3, 540-543 (1979).

Vojinovic “Bromine oxidation and bromine reduction in propylene carbonate” Journal of Electroanalytical Chemistry, 547 (2003) p. 109-113.

Babic et al (Electrochimica Acta, 51, 2006, 3820-3826).

Yoshida et al. (Journal of Electroanalytical Chemistry, 385, 1995, 209-225).

Cuihong Yan et al., The Lastest Research Progress of Electrocatalytic Reduction Product of CO2, Chemical Engineer, Issue 7, p. 42-45, Jul. 25, 2010.

Yingchu Tao et al., Research Progress of Electrochemical Reduction of Carbon Dioxide, Chemistry, Issue 5, p. 272-277, Dec. 31, 2001, http://chemistrymag.org.

Wenying Wei et al., The research progress of CO2 electrocatalysis in water soluble medium, Progress in Chemistry, col. 26, Issue 2, 4 pages, Dec. 2008.

A. Sepulveda-Escribano et al., Platinum catalysts supported on carbon blacks with different surface chemical properties, Applied Catalysis A: General, 173, 1998, p. 247-257.

F.M. Al Kharafi et al., Electrochemical Oxidation of Sulfide Ions on Platinum Electrodes, Modern Applied Science, vol. 4, No. 3, Mar. 2010, pp. 2-11.

P.W.T. Lu, et al., Recent developments in the technology of sulphur dioxide depolarized electrolysis, Journal of Applied Electrochemistry, vol. 11, No. 3, May 1981, pp. 347-355.

Seshadri, Part I Electrocatalysis at modified semiconductor and metal electrodes; Part II Electrochemistry of nickel and cadmium hexacyanoferrates, Diss. Abstr. Int. B 1994, 54(12, Pt. 1), 6198, pp. 52-85.

* cited by examiner

INTEGRATED PROCESS FOR PRODUCING CARBOXYLIC ACIDS FROM CARBON DIOXIDE

CROSS-REFERENCE TO RELATED APPLICATIONS

The present application claims the benefit under 35 U.S.C. §119(e) of U.S. Provisional Application Ser. No. 61/720,670 filed Oct. 31, 2012, U.S. Provisional Application Ser. No. 61/715,060 filed Oct. 17, 2012 and U.S. Provisional Application Ser. No. 61/675,938 filed Jul. 26, 2012. Said U.S. Provisional Application Ser. No. 61/720,670 filed Oct. 31, 2012, U.S. Provisional Application Ser. No. 61,715,060 filed Oct. 17, 2012 and U.S. Provisional Application Ser. No. 61/675,938 filed Jul. 26, 2012 are incorporated by reference in their entireties.

The present application also claims the benefit under 35 U.S.C. §119(e) of U.S. Provisional Application Ser. No. 61/703,158 filed Sep. 19, 2012, U.S. Provisional Application Ser. No. 61/703,229 filed Sep. 19, 2012, U.S. Provisional Application Ser. No. 61/703,175 filed Sep. 19, 2012, U.S. Provisional Application Ser. No. 61/703,231 filed Sep. 19, 2012, U.S. Provisional Application Ser. No. 61/703,232, filed Sep. 19, 2012, U.S. Provisional Application Ser. No. 61/703,234, filed Sep. 19, 2012, U.S. Provisional Application Ser. No. 61/703,238 filed Sep. 19, 2012 and U.S. Provisional Application Ser. No. 61/703,187 filed Sep. 19, 2012. The U.S. Provisional Application Ser. No. 61/703,158 filed Sep. 19, 2012, U.S. Provisional Application Ser. No. 61/703,229 filed Sep. 19, 2012, U.S. Provisional Application Ser. No. 61/703,175 filed Sep. 19, 2012, U.S. Provisional Application Ser. No. 61/703,231 filed Sep. 19, 2012, U.S. Provisional Application Ser. No. 61/703,232, filed Sep. 19, 2012, U.S. Provisional Application Ser. No. 61/703,234, filed Sep. 19, 2012, U.S. Provisional Application Ser. No. 61/703,238 filed Sep. 19, 2012 and U.S. Provisional Application Ser. No. 61/703,187 filed Sep. 19, 2012 are hereby incorporated by reference in their entireties.

The present application incorporates by reference U.S. patent application Ser. No. 13/724,878 filed on Dec. 21, 2012, now U.S. Pat. No. 8,647,493, U.S. patent application Ser. No. 13/724,647 filed Dec. 21, 2012, now U.S. Pat. No. 8,845,876, U.S. patent application Ser. No. 13/724,231 filed on Dec. 21, 2012, now U.S. Pat. No. 8,845,875, U.S. patent application Ser. No. 13/724,807 filed on Dec. 21, 2012, now U.S. Pat. No. 8,692,019, U.S. patent application Ser. No. 13/724,996 filed on Dec. 21, 2012, now U.S. Pat. No. 8,691,069, U.S. patent application Ser. No. 13/724,719 filed on Dec. 21, 2012, U.S. patent application Ser. No. 13/724,082 filed on Dec. 21, 2012, now U.S. Pat. No. 8,821,709, and U.S. patent application Ser. No. 13/724,768 filed on Dec. 21, 2012, now U.S. Pat. No. 8,444,844 in their entireties.

TECHNICAL FIELD

The present disclosure generally relates to the field of electrochemical reactions, and more particularly to methods and/or systems for producing carboxylic acids from carbon dioxide.

BACKGROUND

The combustion of fossil fuels in activities such as the electricity generation, transportation, and manufacturing produces billions of tons of carbon dioxide annually. Research since the 1970s indicates increasing concentrations of carbon dioxide in the atmosphere may be responsible for altering the Earth's climate, changing the pH of the ocean, and other potentially damaging effects. Countries around the world, including the United States, may be seeking ways to mitigate emissions of carbon dioxide.

One implementation may be to convert carbon dioxide into economically valuable materials such as fuels and industrial chemicals. If the carbon dioxide may be converted using energy from renewable sources, it will be possible to both mitigate carbon dioxide emissions and to convert renewable energy into a chemical form that may be stored for later use. Electrochemical and photochemical pathways may be likely mechanisms for carbon dioxide conversion.

SUMMARY OF THE PREFERRED EMBODIMENTS

The present disclosure is a method and system for production of carboxylic based chemicals, including carboxylic acids and salts. A method for producing at oxalic acid may include receiving an anolyte feed at an anolyte region of an electrochemical cell including an anode and receiving a catholyte feed including carbon dioxide and an alkali metal hydroxide at a catholyte region of the electrochemical cell including a cathode. The method may include applying an electrical potential between the anode and cathode sufficient to reduce the carbon dioxide to at least one reduction product and converting the at least one reduction product and the alkali metal hydroxide to an alkali metal oxalate via a thermal reactor. The method may further include receiving the alkali metal oxalate at an electrochemical acidification electrolyzer and converting the alkali metal oxalate to oxalic acid at the electrochemical acidification electrolyzer.

It is to be understood that both the foregoing general description and the following detailed description are exemplary and explanatory only and are not necessarily restrictive of the present disclosure. The accompanying drawings, which are incorporated in and constitute a part of the specification, illustrate subject matter of the disclosure. Together, the descriptions and the drawings serve to explain the principles of the disclosure.

BRIEF DESCRIPTION OF THE DRAWINGS

The numerous advantages of the present disclosure may be better understood by those skilled in the art by reference to the accompanying figures in which.

DETAILED DESCRIPTION

Reference will now be made in detail to the subject matter disclosed, which is illustrated in the accompanying drawings.

The present disclosure a method and system for production of carboxylic based chemicals, including carboxylic acids and salts. The method may employ an electrochemical cell reaction to produce carbon monoxide, CO, or sodium formate from a carbon dioxide feedstock. A thermal reaction with an alkali metal hydroxide, may be used to combine, for example, two sodium formate molecules, into a sodium oxalate product. The sodium oxalate may be then converted to an oxalic acid by a membrane based electrochemical acidification process, where protons ($H^+$ ions) formed at the anode may be used to replace the sodium ions, and the sodium ions may be captured as sodium hydroxide at the cathode, and may be recycled to be used as the alkali metal hydroxide used in the intermolecular condensation process unit operation.

Before any embodiments of the disclosure are explained in detail, it is to be understood that the embodiments may not be limited in application per the details of the structure or the function as set forth in the following descriptions or illustrated in the figures. Different embodiments may be capable of being practiced or carried out in various ways. Also, it is to be understood that the phraseology and terminology used herein is for the purpose of description and should not be regarded as limiting. The use of terms such as "including," "comprising," or "having" and variations thereof herein are generally meant to encompass the item listed thereafter and equivalents thereof as well as additional items. Further, unless otherwise noted, technical terms may be used according to conventional usage. It is further contemplated that like reference numbers may describe similar components and the equivalents thereof.

Figure 1A:
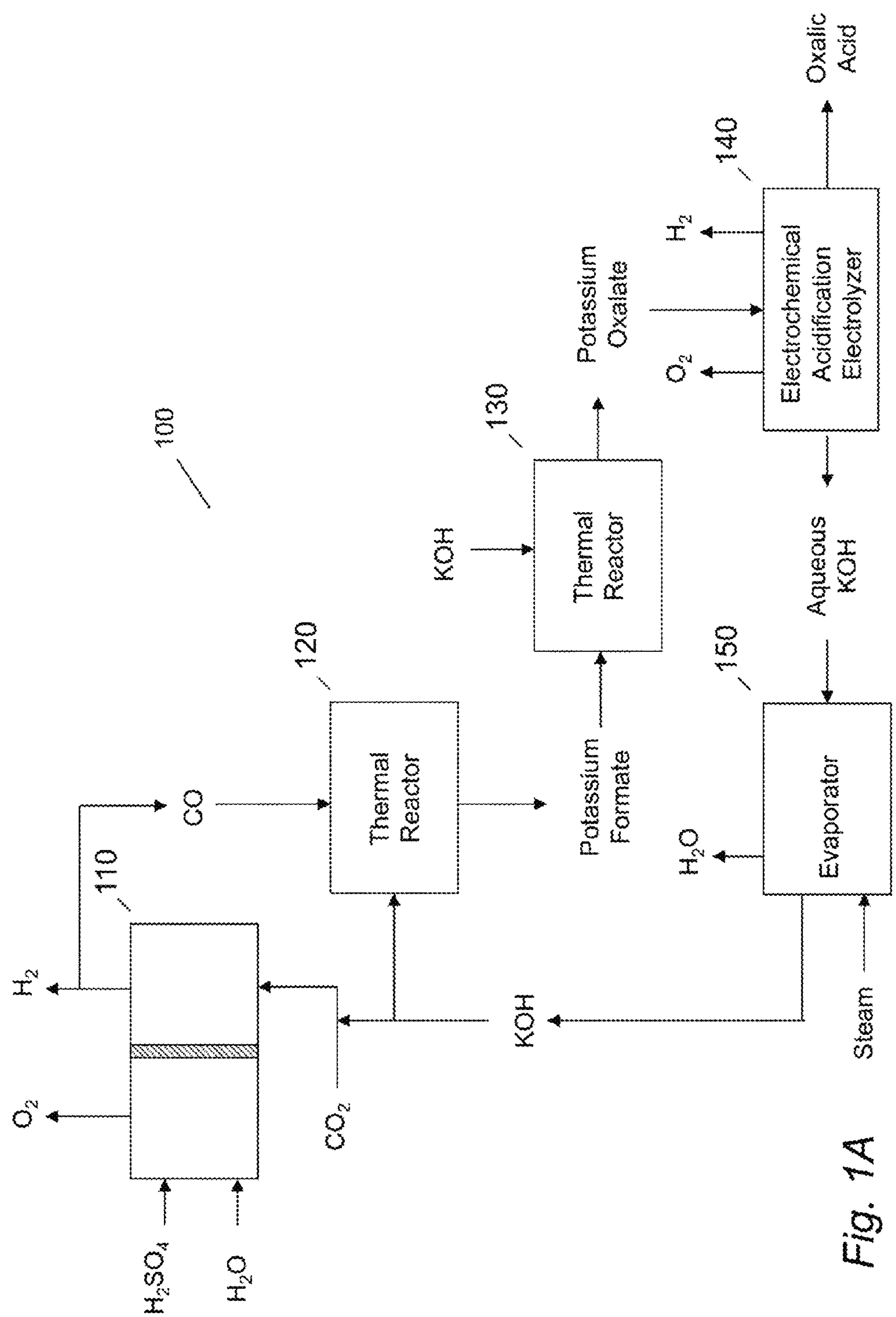
FIG. 1A shows a system for production of oxalic acid starting with the electrochemical generation of carbon monoxide from carbon dioxide in accordance with an embodiment of the present disclosure.

Referring to FIG. 1A, a system 100 for production of dicarboxylic acid, such as oxalic acid starting with the electrochemical generation of formate from carbon dioxide in accordance with an embodiment of the present disclosure is shown. System 100 may include an electrochemical cell 110. Electrochemical cell 110 (also referred as a container, electrolyzer, or cell) may be implemented as a divided cell. The divided cell may be a divided electrochemical cell and/or a divided photo-electrochemical cell. Electrochemical cell 110 may include an anolyte region and a catholyte region. Anolyte region and cathoyte region may refer to a compartment, section, or generally enclosed space, and the like without departing from the scope and intent of the present disclosure.

Catholyte region may include a cathode. Anolyte region may include an anode. An energy source (not shown) may generate an electrical potential between the anode and the cathode of electrochemical cell 110. The electrical potential may be a DC voltage. Energy source may be configured to supply a variable voltage or constant current to electrochemical cell 110. A separator may selectively control a flow of ions between the anolyte region and the catholyte region. Separator may include an ion conducting membrane or diaphragm material.

Electrochemical cell 110 may operate to perform an electrochemical reduction of carbon dioxide in an electrochemical cell producing carbon monoxide (CO) and hydrogen as cathode products and oxygen as an anode product when using sulfuric acid ($H_2SO_4$) as an anolyte.

The CO generated from electrochemical cell 110 may be separated from the hydrogen and then passed to a thermal reactor 120. Thermal reactor may react the carbon monoxide with an alkali metal hydroxide, such as KOH via a thermal intermolecular condensation reaction to form potassium formate. Thermal reactor 120 may operate to perform a thermal decomposition reaction or a carbonylation reaction, which may be reactions which incorporate CO into organic and inorganic chemical structures.

Potassium formate formed from thermal reactor 120 may be passed to another thermal reactor 130. Thermal reactor 130 may perform a second similar thermal intermolecular condensation reaction with an alkali metal hydroxide (e.g. KOH) that may promote the reaction to produce potassium oxalate. While system 100 of FIG. 1 depicts a thermal reactor 120 and thermal reactor 130, it is contemplated that a single thermal reactor may be employed with system 100 without departing from the scope and intent of the present disclosure.

Potassium oxalate from thermal reactor 130 may be dissolved in water and may be passed to an electrochemical acidification electrolyzer 140. Electrochemical acidification electrolyzer 140 may produce a dicarboxylic acid, such as oxalic acid, and KOH along with oxygen and hydrogen byproducts. Electrochemical acidification electrolyzer 140 may be a membrane based unit including of at least three regions, including an anode region, one or more central ion exchange regions, and a cathode region. It is contemplated that an energy source (not shown) may generate an electrical potential between the anode and the cathode of electrochemical acidification electrolyzer 140 sufficient to produce oxalic acid. Potassium oxalate may be passed through the central ion exchange region where potassium ions may be replaced with protons, and the displaced potassium ions pass through the adjoining membrane into the cathode region to form KOH. The anode reaction may utilize an acid, such as sulfuric acid, producing oxygen and hydrogen ions.

The hydrogen byproduct resulting from electrochemical acidification electrolyzer 140, as an alternative embodiment, may be used as a fuel to produce steam or used in a side chemical process that may utilize hydrogen, such as in a chemical hydrogenation process.

The dicarboxylic acid, such as an oxalic acid product may be purified to produce a final purified product, or may be further processed as a chemical intermediate to produce another product, such as monoethylene glycol, using an electrochemical reduction or a thermochemical process.

Aqueous KOH from electrochemical acidification electrolyzer 140 may be passed to an evaporator 150. Evaporator 150 may evaporate the water from aqueous KOH product using steam or another heat source, converting it into a concentrated aqueous solution and/or solid with 5% or less water content as needed in electrochemical cell 110 and thermal reactor 120.

Figure 1B:
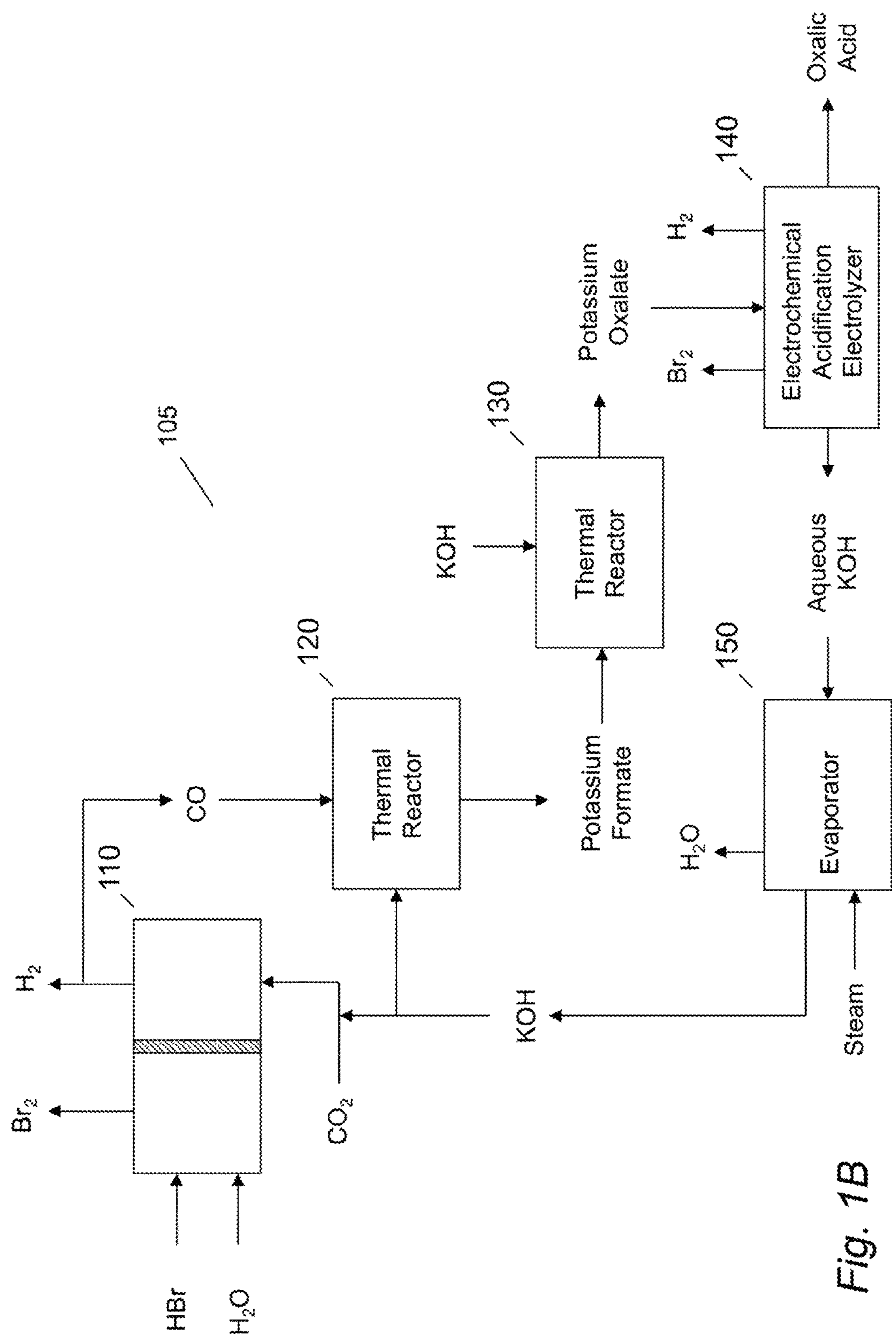
FIG. 1B shows a system for the production of oxalic acid utilizing HBr in the anolyte to co-produce bromine in accordance with an embodiment of the present disclosure.

Referring to FIG. 1B, a system 105 for production of dicarboxylic acid, such as oxalic acid, utilizing a hydrogen halide, such as HBr, in the anolyte to co-produce bromine in accordance with an embodiment of the present disclosure is shown. System 105 may operate with a less energy intensive electrochemical process, using HBr as the anolyte in the anode region of electrochemical cell 110 and electrochemical acidification electrolyzer 140, producing bromine and hydrogen ions at a significantly lower anode potential. The bromine may then be used, for example, in reactions to produce brominated chemical products, such as brominated organic compounds, for example bromoethane, which may then be converted into alcohols such as ethanol, or converted to monoethylene glycol in a series of thermochemical reactions. It is contemplated that system 105 shown with thermal reactor 120 and thermal reactor 130 could be implemented with a single thermal reactor without departing from the scope and intent of the present disclosure.

Figure 2A:
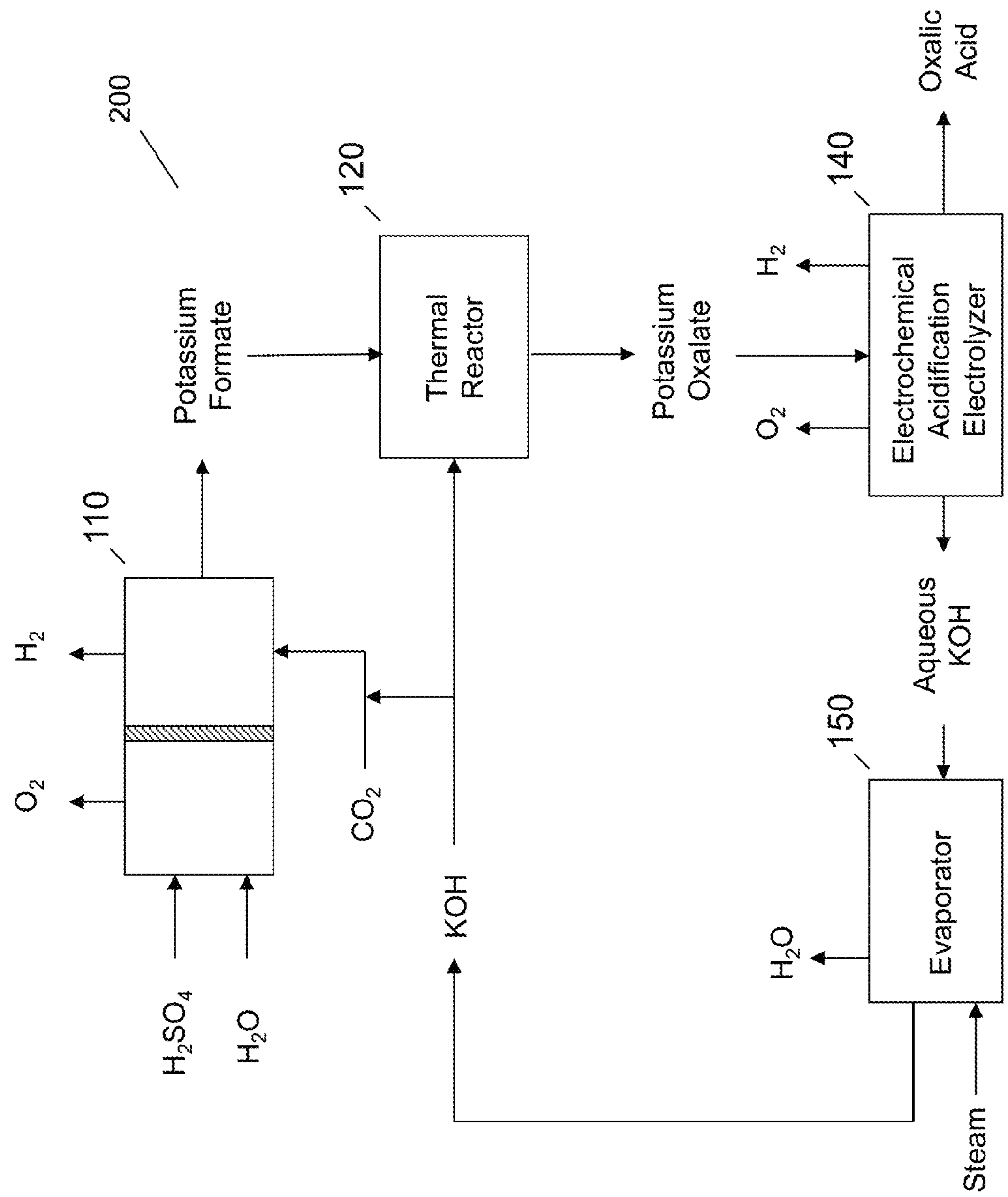
FIG. 2A shows a system for production of oxalic acid starting with the electrochemical generation of formate using carbon dioxide in accordance with an embodiment of the present disclosure.

Referring to FIG. 2A, a system 200 for production of dicarboxylic acid, such as oxalic acid, starting with the electrochemical generation of formate using carbon dioxide in accordance with an embodiment of the present disclosure is shown. System 200 may provide an alternative system for production of oxalic acid as produced by systems 100, 105 of FIG. 1A and FIG. 1B.

System 200 may include an electrochemical cell 110. Electrochemical cell 110 may operate to perform an electrochemical reduction of carbon dioxide with a potassium carbonate cathode feed, which may be formed from the reaction of $CO_2$ with KOH, to produce potassium formate along with oxygen as an anode product when using sulfuric acid ($H_2SO_4$) as an anolyte.

Potassium formate may be passed to a thermal reactor 120. Thermal reactor 120 may perform a thermal intermolecular condensation reaction with an alkali metal hydroxide (e.g. KOH) to produce potassium oxalate.

Potassium oxalate from thermal reactor 120 may be dissolved in water and may be passed to an electrochemical acidification electrolyzer 140. Electrochemical acidification electrolyzer 140 may produce dicarboxylic acid, such as oxalic acid, and KOH along with oxygen and hydrogen byproducts. Electrochemical acidification electrolyzer 140 may be a membrane based unit including of at least three regions, including an anode region, one or more central ion exchange regions, and a cathode region. Potassium oxalate may be passed through the central ion exchange region where potassium ions may be replaced with protons, and the displaced potassium ions pass through the adjoining membrane into the cathode region to form KOH. The anode reaction may utilize an acid, such as sulfuric acid, producing oxygen and hydrogen ions.

The hydrogen byproduct resulting from electrochemical acidification electrolyzer 140, as an alternative embodiment, may be used as a fuel to produce steam or used in a side process that may utilize hydrogen, such as in a chemical hydrogenation process.

The dicarboxylic acid, such as oxalic acid product may be purified to produce a final purified product, or may be further processed as a chemical intermediate to produce another product, such as monoethylene glycol, using an electrochemical reduction or thermochemical process.

Aqueous KOH from electrochemical acidification electrolyzer 140 may be passed to an evaporator 150. Evaporator 150 may evaporate the water from aqueous KOH product using steam or another heat source, converting it into a concentrated aqueous solution and/or solid with 5% or less water content as needed in the electrochemical cell 110 or thermal reactor 120.

Figure 2B:
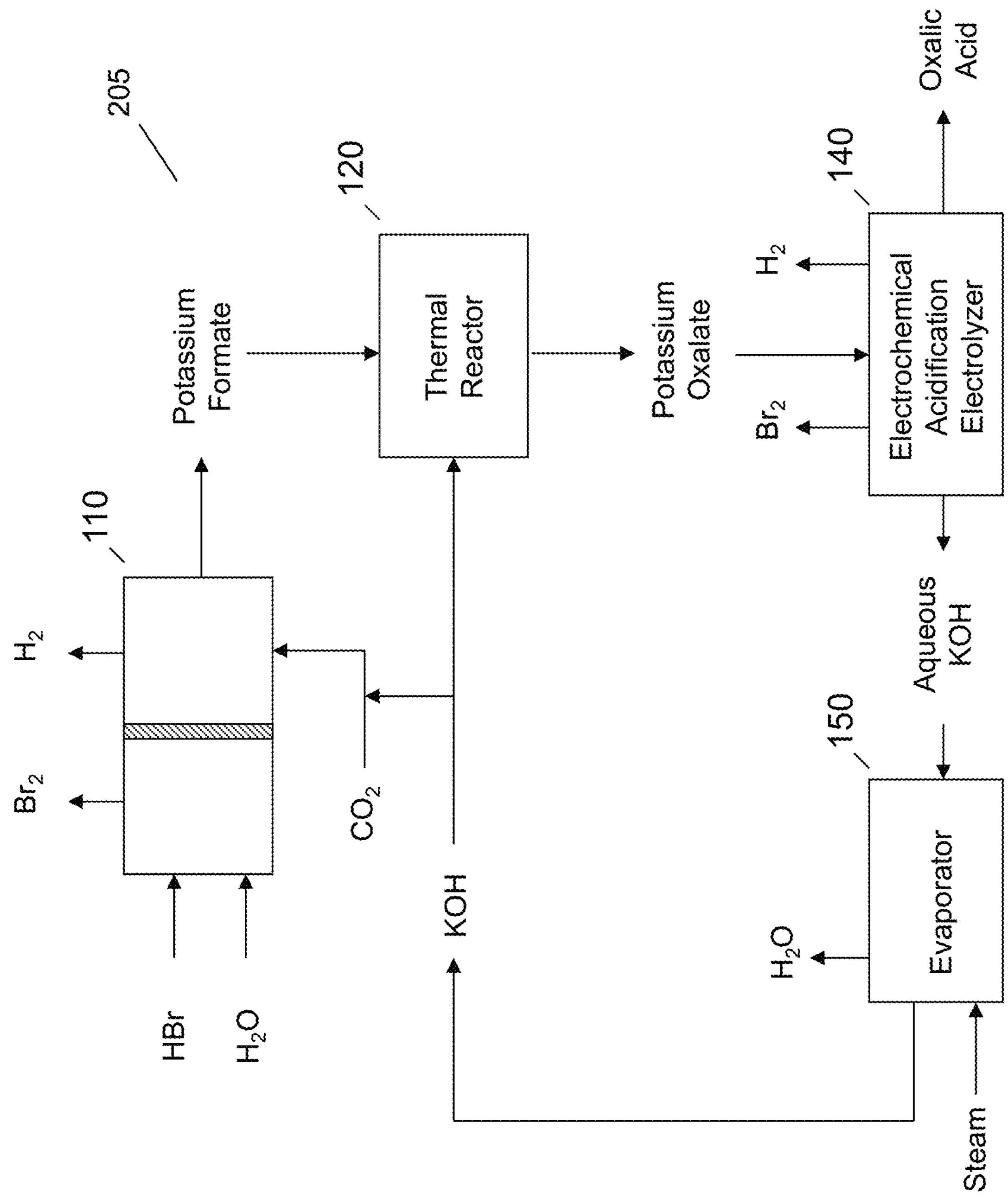
FIG. 2B shows a system for production of oxalic acid via electrochemical generation of formate using carbon dioxide and utilizing a halogen halide in the anolyte to co-produce bromine in accordance with an embodiment of the present disclosure.

Referring to FIG. 2B, a system 205 for production of oxalic acid dicarboxylic acid, such as oxalic acid via electrochemical generation of formate using carbon dioxide and utilizing a halogen halide in the anolyte to co-produce a halogen, such as bromine, in accordance with an embodiment of the present disclosure is shown. System 205 may be similar to system 200, where system 205 may use a hydrogen halide, such as HBr as the anolyte in the anode regions of electrochemical cell 110 and electrochemical acidification electrolyzer 140. Electrochemical cell 110 may produce bromine and hydrogen ions at a significantly lower anode potential. Bromine may then be used, for example, in reactions to produce brominated chemical products, such as bromoethane, which may then be converted into alcohols such as ethanol, or converted to monoethylene glycol in a series of thermochemical reactions.

Figure 3:
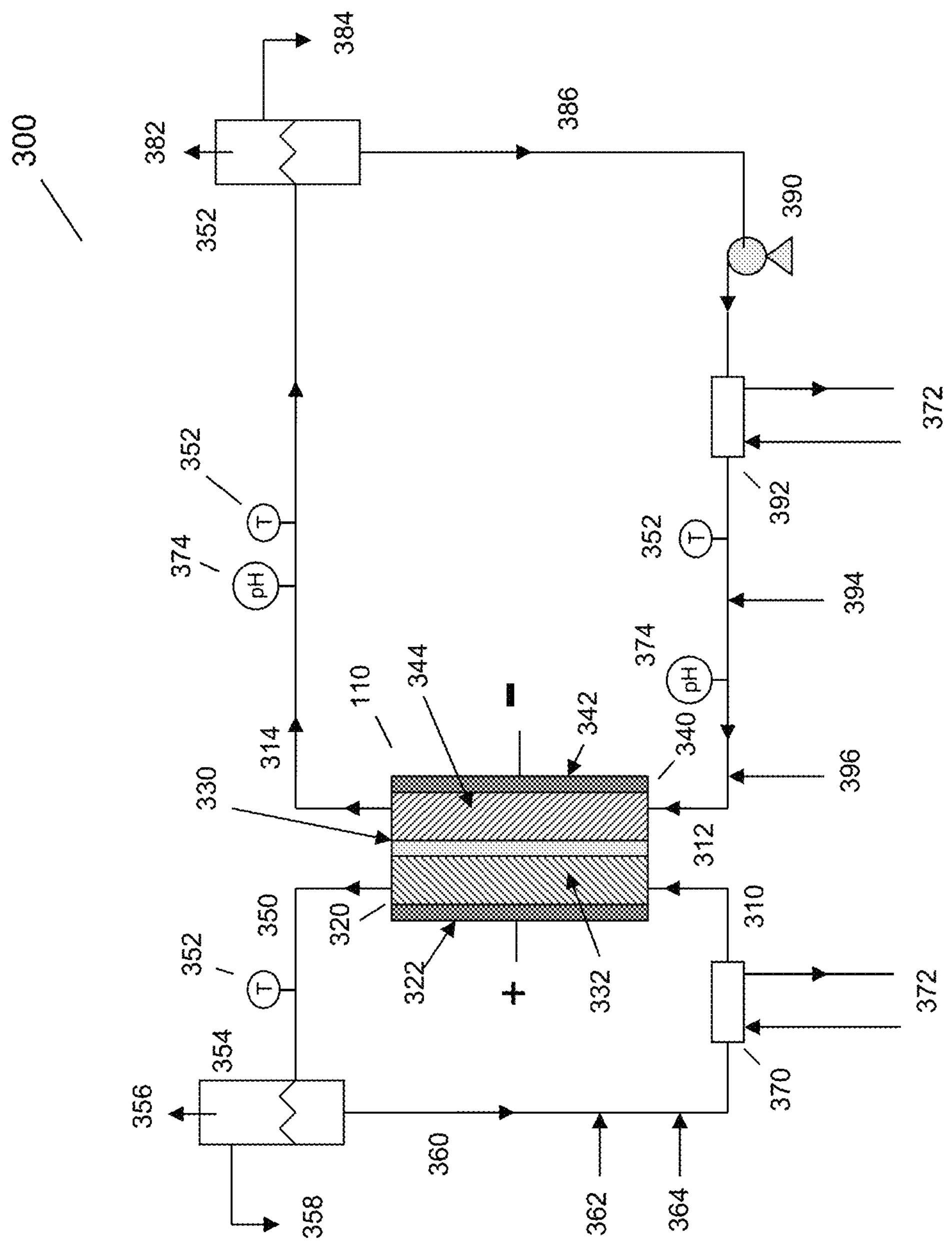
FIG. 3 shows a system for formation of potassium formate using carbon dioxide in accordance with an embodiment of the present disclosure.

Referring to FIG. 3, a system 300 for production of a formate, such as potassium formate, using carbon dioxide in accordance with an embodiment of the present disclosure is shown. System 300 may illustrate the electrochemical reduction of carbon dioxide in the production of an alkali metal formate as shown in electrochemical cell 110 of FIG. 2A and FIG. 2B. Electrochemical cell 110 may include an anolyte input feed 310 and a catholyte input feed 312 to produce a product 314. Product 314 may be a solution of potassium formate with an excess potassium bicarbonate ($KHCO_3$). Anolyte region 320 may have a titanium anode 322 having an anode electrode catalyst coating facing cation exchange membrane 330. Anode mesh screen 332 may be a folded expanded titanium screen with an anode electrocatalyst coating and provides spacing and contact pressure between anode 322 and cation exchange membrane 332. Cation exchange membrane 330 may selectively control a flow of ions between anolyte region 320 from catholyte region 340.

Catholyte region 340 may have a mounted cathode 342, which may be a metal electrode with an active electrocatalyst layer on the front side facing membrane 330. High surface area cathode structure 344 may be mounted with direct contact pressure between the face of cathode 342 and cation membrane 330.

As shown in FIG. 1A and FIG. 2A, feeding anolyte region 320 may be stream 310 which may include anolyte, the anolyte including an aqueous sulfuric acid electrolyte solution. Stream 310 may enter the anolyte region 320 and flow by the face of anode 322 through folded anode screen 332. Anode reactions may typically be water splitting into oxygen ($O_2$) and hydrogen ions ($H^+$) or protons. The gases and liquid mixture from anolyte region 320 may leave as stream 350, which flows by temperature sensor 352 monitoring a solution temperature in the stream, and into anolyte gas/liquid disengager 354. In disengager 354, the gas may be vented as stream 356, and excess anolyte overflow leaves as stream 358. Stream 360 may be a gas-depleted exit stream from the anolyte disengager 354, with a deionized water feed stream 362 and a sulfuric acid make-up feed stream 364 added to the recirculation stream to maintain anolyte acid strength and volume. Stream 360 with added streams 362 and 364 may then pass through an optional heat exchanger 370 with a cooling water supply 372, and then becomes stream 310 feeding into the anolyte region 320.

Electrochemical cell 110 may include a catholyte region 340 which includes cathode 342 having an electrocatalyst surface facing membrane 330. High surface area cathode structure 344 may be mounted between membrane 330 and cathode 342, relying on contact pressure with cathode 342 for conducting electrical current into the structure. The interface between high surface area structure 344 and membrane 330 may utilize a thin expanded plastic mesh insulator screen (not shown) to minimize direct contact with the high surface area cathode material with the membrane 330.

Feed stream 312 may feed into catholyte region 340, flowing through the high surface area structure 344 and across the face of cathode 342 where cathode reduction reactions between carbon dioxide, electrolyte, and cathode material at the applied current and voltage potential produce exit stream 314, the exit stream including a formate.

Stream 314 may be the exit solution and gas mixture product from the cathode reaction which flows by pH monitoring sensor 374 and temperature sensor 352 and then into catholyte gas/liquid disengager 380 where the gas exits as stream 382 and formate/electrolyte overflow exits as stream 384, and the gas-depleted stream leaves the disengager as stream 386. Stream 386 may then enter an input of catholyte recirculation pump 390, which then passes through heat exchanger 392 which uses cooling water 372, then passes by temperature sensor 352. A fresh catholyte electrolyte feed 394 may be metered into stream 386 which may be used to adjust the catholyte flow stream pH into the catholyte region 340 and control a product overflow rate and sets the formate product concentration, with the pH monitored by pH sensor 374. Carbon dioxide flow stream 396 may be metered into the flow stream which enters the catholyte region 340 as stream 312.

In an alternative embodiment, as shown in FIGS. 1B and 2B, the sulfuric acid anolyte shown in FIGS. 1A and 2A may be replaced with a hydrogen halide (e.g. HBr) as the anolyte, producing a halide (e.g. bromine) and hydrogen ions at a much lower voltage potential than the generation of oxygen at the anode. The halide may then be used, for example, in reactions to produce halide chemical products, such as bromoethane in the reaction with an alkane, such as ethane, which may then be converted into alcohols (e.g. ethanol) or converted to monoethylene glycol in a series of thermochemical reactions.

Figure 4:
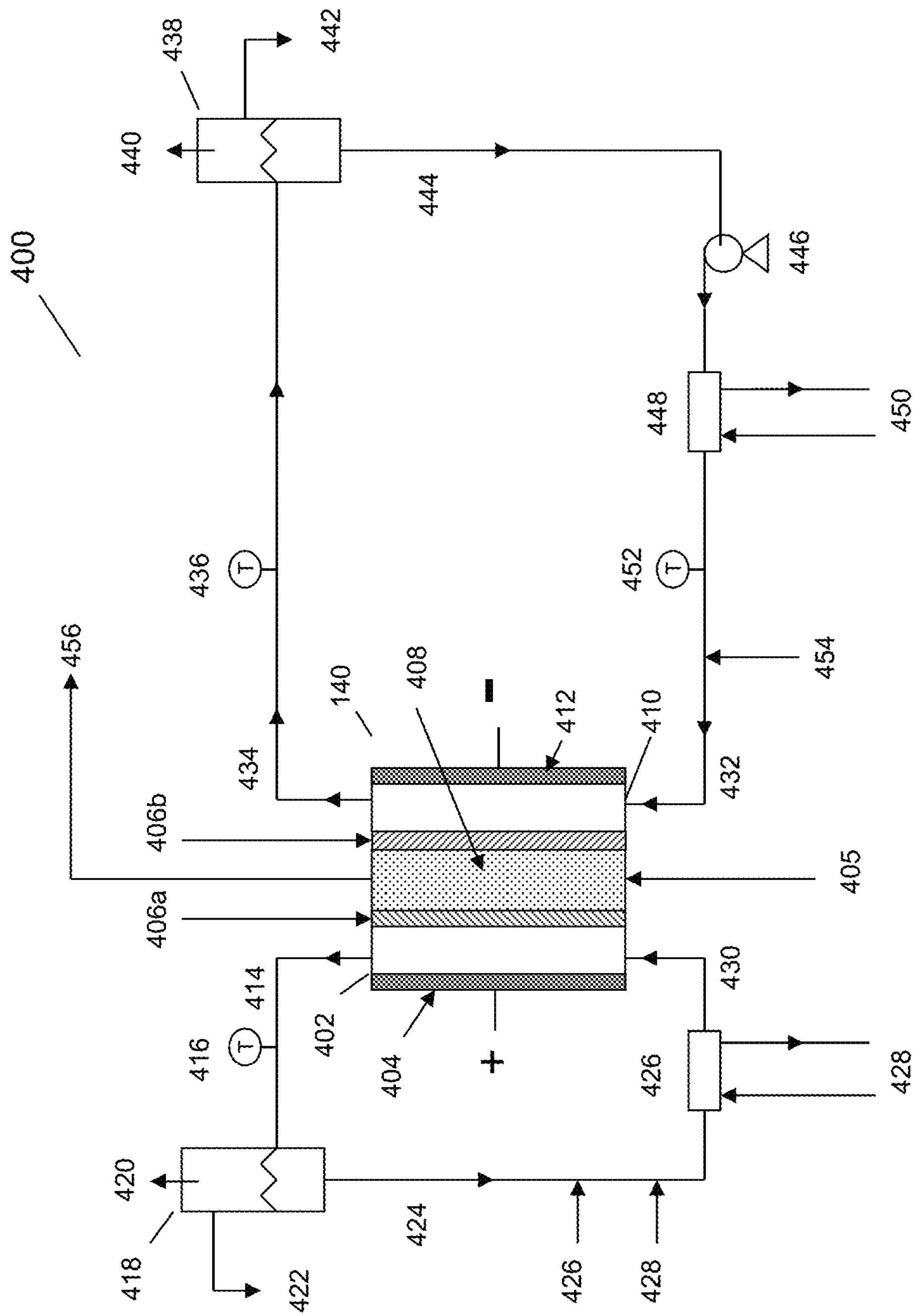
FIG. 4 shows a system for electrochemical acidification of potassium oxalate in accordance with an embodiment of the present disclosure.

Referring to FIG. 4, system 400 for electrochemical acidification of potassium oxalate in accordance with an embodiment of the present disclosure is shown. Electrochemical acidification electrolyzer 140 may include an anolyte region 402, a central ion exchange region 408 bounded by cation ion exchange membranes 406*a* and 406*b* on each side, and a catholyte region 410 where an alkali metal hydroxide (e.g. KOH) may be formed. Hydrogen ions ($H^+$) or protons may be generated in the anolyte region 402, which then may pass through the adjoining membrane 406*a* into the central ion exchange region 408 when a potential and current may be applied to the cell. An alkali metal oxalate (e.g. potassium oxalate) product solution 405, such as generated in thermal reactor 120, 130 of FIG. 1A-2B, may pass through the central ion exchange region 408, where the protons displace the potassium ions in the solution stream, thus acidifying the solution and forming a dicarboxylic acid, such as oxalic acid, stream 456, and the displaced potassium ions may pass through the adjoining cation exchange membrane 406*b* into the catholyte region 410, where they combine with hydroxide ions ($OH^-$) formed from water reduction reaction at the cathode to form an alkali metal hydroxide (e.g. KOH) stream 434.

Electrochemical acidification electrolyzer 140 may include input feeds 430 and 432 and may produce a solution of a dicarboxylic acid (e.g. oxalic acid) 456, oxygen 420 from the anolyte region 402, and KOH 442 from the anolyte region 410. Anode region 402 may include a titanium anode 404 with an anode electrode catalyst coating facing cation exchange membrane 406*a*. The central ion exchange region 408 may contain a plastic mesh spacer to maintain the space in the central ion exchange region between cation exchange membranes 406*a* and 406*b*. Optionally, a preferred material may be the use of a cation ion exchange material between the membranes, so that there may be increased electrolyte conductivity in the ion exchange region solution. Catholyte region 410 may include a cathode 412.

Anolyte region 402 may have feed stream input 430 including sulfuric acid, which may flow through the anolyte region 402 and exit as stream 414 including a gas and liquid, passing by temperature sensor 416 into anolyte disengager 418, where the gas exits as stream 420 and liquid overflow as stream 422. Gas-depleted stream 424 may exit the anolyte disengager 418 and deionized water stream 426 may be metered into the stream 424 as well as sulfuric acid make-up stream 428 to maintain acid electrolyte strength in the anolyte region 402. Stream 424 may pass through optional heat exchanger 426 which may have cooling water supply 428 to cool or maintain the stream 424 temperature, and the stream 424 enters the anolyte region 402 as stream 430.

Catholyte region 410 may include feed stream 432 which may be the recirculating alkali metal hydroxide (e.g. KOH) in the catholyte loop, which enters catholyte region 410 and flows by cathode 412, which may generate hydrogen gas and hydroxide ($OH^-$) ions, and forms a alkali metal hydroxide from the combination of alkali metal ions crossing the membrane 406*b* with the hydroxide ions formed at the cathode 412 from the reduction of water. Exit stream 434 from the cathode region 410 may contain alkali metal hydroxide and hydrogen gas from the cathode reactions, and passes by temperature sensor 436 and then into catholyte disengager 438, where hydrogen gas 440 may be separated from the catholyte solution, which exits catholyte disengager 438 as recycle stream 444 and alkali metal hydroxide product overflow stream 442. Recycle stream 444 may pass through optional recirculation pump 446 and then through optional heat exchanger 448, which uses cooling water supply 450. The stream then passes by temperature sensor 452, and then may have a deionized water addition stream 454 added to the stream to control the alkali metal hydroxide concentration in the catholyte recirculation loop, and then reenters the catholyte region 410 as stream 432.

In an alternative embodiment, the sulfuric acid anolyte may be replaced using HBr as the anolyte, producing bromine and hydrogen ions at a much lower voltage potential than the generation of oxygen at the anode.

Formate $CO_2$ Reduction Chemistry

The postulated chemistry of the reduction of $CO_2$ at the cathode may be as follows.

Hydrogen atoms may be adsorbed at the electrode from the reduction of water as shown in equation (1).

$$H^+ + e^- \rightarrow H_{ad} \quad (1)$$

Carbon dioxide may be reduced at the cathode surface with the adsorbed hydrogen atom to form formate, which may be adsorbed on the surface as in equation (2).

$$CO_2 + H_{ad} \rightarrow HCOO_{ad} \quad (2)$$

The adsorbed formate adsorbed on the surface then reacts with another adsorbed hydrogen atom to form formic acid that may be released into the solution as in equation (3)

$$HCOO_{ad} + H_{ad} \rightarrow HCOOH \quad (3)$$

The competing reaction at the cathode may be the reduction of water where hydrogen gas may be formed as well as hydroxide ions as in equation (4).

$$2H_2O + 2e^- \rightarrow H_2 + 2OH^- \quad (4)$$

In observations of the operation of the electrochemical cells in the present system, the addition of bicarbonate in the catholyte solution and utilizing an acidic anolyte, it was noted that the pH of the catholyte solution declines with time, and two types of bubbles may be seen in the catholyte output stream—large bubbles and a lower concentration of very fine bubbles in the output stream of the catholyte region. It may be postulated that the large bubbles may be composed of $CO_2$ from the proton or hydrogen ion decomposition of bicarbonate to $CO_2$ and water and that the very fine bubbles may be byproduct hydrogen. It may be postulated that the hydrogen ions or protons passing through the membrane may be decomposing some of the bicarbonate to $CO_2$ and water within the electrode material, and possibly very close to the electrode surfaces, providing a higher $CO_2$ partial pressure environment, and resulting in higher current efficiencies at low operating partial pressures of dissolved $CO_2$ in the solution at ambient operating pressures.

Operating the electrochemical cell at higher pressures (above atmospheric), should also increase the current efficiency and allow operation of the cells at higher current densities.

Anode Reactions

The anode reaction may be the oxidation of water into oxygen and hydrogen ions as shown in equation (5).

$$2H_2O \rightarrow 4H^+ + 4e^- + O_2 \quad (5)$$

Below may be the various preferred and alternative embodiments for the process, arranged in different categories.

Formate Formation From CO

The thermal intermolecular reaction of potassium formate CO with KOH may be as follows:

$$CO + KOH \rightarrow HCOOK \quad (6)$$

The KOH may be consumed in the reaction. Under the right conditions, both formate and oxalate may both be produced, and which may decrease the number of process steps. The production of both would require the separation of these carboxylic acids from each other.

Carbon monoxide may also be selectively absorbed in a alkali metal carbonate and bicarbonate aqueous solutions to produce formate, where M is an alkali metal which may be as follows:

$$CO + MHCO3 \rightarrow MOOCH + CO_2 \quad (7)$$

$$2CO + M_2CO_3 + H_2O \rightarrow 2MCOCH + CO_2 \quad (8)$$

These reactions may not require MOH, such as NaOH or KOH, in the reaction for the formation of M-formate.

Oxalate From Formate

The thermal intermolecular reaction of potassium formate with KOH may be as follows:

$$2HCOOK + KOH \rightarrow K_2C_2O_4 + H_2 \quad (9)$$

Sodium or potassium carbonate may also be used for converting formate to oxalate, but the yields have been shown to be significantly lower. Under the right operating conditions, the yields may be significantly improved.

Anode Oxidation Reactions

The anode reaction when utilizing sulfuric acid in the anolyte, may be the oxidation of water generating hydrogen ions and oxygen as follows:

$$2H_2O \rightarrow O_2 + 4H^+ + 4e^- \quad (10)$$

If hydrobromic acid, HBr, may be used in the anolyte, the reaction may be the oxidation of the bromide to bromine as follows:

$$2HBr \rightarrow Br_2 + 2H^+ + 2e^- \quad (11)$$

Electrolyzer Configurations

The following present various exemplary combinations of cell configurations, electrode structures, and anolyte/catholyte compositions that may be used in the electrochemical CO and/or formate, and electrochemical acidification (EA) electrolyzers in the above described processes.

The cathode of the electrochemical cell 110 and electrochemical acidification electrolyzer 140 may be a high surface area electrode. The void volume for the cathode may be from about 30% to 98%. The surface area of the cathode may be from 2 $cm^2/cm^3$ to 500 $cm^2/cm^3$ or higher. The surface areas may be further defined as a total area in comparison to the current distributor/conductor back plate area with a preferred range of from 2 to 1000 times the current distributor/conductor back plate area.

The cathode of the electrochemical cell 110 may be electrolessly plated indium or tin on a copper woven mesh, screen or fiber structure. Indium-copper intermetallics may be formed on the copper woven mesh, screen or fiber structure. The intermetallics may be harder than the soft indium metal, and allow better mechanical properties in addition to usable catalytic properties.

In the electrochemical reduction of carbon dioxide metals including Pb, Sn, Hg, Tl, In, Bi, and Cd among others may produce formic acid (or formate) as a major $C_1$ product in aqueous solutions. Alloy combinations of these metals such as Hg/Cu, Sn—Cd, Sn—Zn, Cu—Sn, may form at various performance efficiencies. One of the issues may be that a number of these metals, such as Sn and Cu, may be that the surface changes and deactivates or loses the Faradaic conversion activity in producing formate. The surface then may have to be reactivated by a reverse current or polarity. In the production for formation of $C_{2+}$ chemicals, such as oxalic acid and glycolic acid, metals such as Ti, Nb, Cr, Mo, Ag, Cd, Hg, Tl, An, and Pb as well as Cr—Ni—Mo steel alloys among many others may result in the formation of these higher $C_{2+}$ products.

In another embodiment, the cathode surfaces may be renewed by the periodic addition of indium salts or a mix of indium/tin salts in situ during the electrochemical cell operation. Electrochemical cell 110 may be operated at full rate during operation, or temporarily operated at a lower current density with or without any carbon dioxide addition during the injection of the metal salts.

In another exemplary embodiment, in preparing cathode materials for the production of $C_{2+}$ chemicals, the addition of metal salts that may reduce on the surfaces of the cathode structure may be also used, such as the addition of Ag, Au, Mo, Cd, Sn, etc. to provide a catalytic surface that may be difficult to prepare directly during cathode fabrication or for renewal of the catalytic surfaces.

Cathode 412 for the electrochemical acidification electrolyzer 140 may include stainless steels and nickel electrodes. Cathode 412 may include coatings on the cathode to reduce the hydrogen overpotential.

An alkali metal hydroxide range for the electrochemical acidification electrolyzer 140 may be 5% to 50% by weight, and more preferably 10% to 45% by weight. The alkali metal hydroxide examples may be NaOH, KOH, CsOH and the like.

Cathode materials for the cathode of electrochemical cell 110 for carbon monoxide production from $CO_2$ may include precious and noble metals, Cu, Ag, Au, and their oxides, specifically the oxides of copper. Other d-block metals, such as Zn and Ni, may be selective for CO reduction in aqueous media. Regardless of specificity for CO as a $CO_2$ reduction product, a cathode for electrochemical cell 110 for an aqueous system for $CO_2$ reduction to CO may have a high hydrogen overpotential to prevent competing $H_2$ formation.

Anions used for CO production at the cathode may be any species stable at working potentials such as sulfate, chloride or bicarbonate. $CO_2$ reduction to CO may favor high pH due to limited competing $H_2$ formation; however there may be a practical pH maximum at around 8.5 for a saturated $CO_2$ solution due to the formation of carbonic acid on dissolution. There may be no strict lower limit that may have been observed. Depending on the chemistry of the system, the pH of the catholyte region of electrochemical cell 110 may range from 3 to 12. The pH may be a function of the catalysts used, such that there is no corrosion at the electrochemical cell 110 and catholyte operating conditions.

Electrolytes for the electrochemical cell 110 for forming CO and formates may include alkali metal bicarbonates, carbonates, sulfates, and phosphates, borates, ammonium, hydroxides, chlorides, bromides, and other organic and inorganic salts. The electrolytes may also include non-aqueous electrolytes, such as propylene carbonate, methanesulfonic acid, methanol, and other ionic conducting liquids, which may be in an aqueous mixture, or as a non-aqueous mixture in the catholyte. The introduction of micro bubbles of carbon dioxide into the catholyte stream may improve carbon dioxide transfer to the cathode surfaces.

Electrolytes for the anolyte region of the electrochemical cell 110 may include: alkali metal hydroxides, (e.g. as KOH, NaOH, LiOH) in addition to ammonium hydroxide; inorganic acids such as sulfuric, phosphoric, and the like; organic acids such as methanesulfonic acid in both non-aqueous and aqueous solutions; and alkali halide salts, such as the chlorides, bromides, and iodine types such as NaF, NaCl, NaBr, LiBr, KF, KCl, Kbr, KI, and NaI, as well as their acid halide forms, such as HCl, and HBr. The alkali halide salts may produce, for example, fluorine, chlorine, bromine, or iodine as halide gas or dissolved aqueous products from the anolyte region. Methanol or other hydrocarbon non-aqueous liquids may also be used, and they would form some oxidized organic products from the anolyte. Selection of the anolyte would be determined by the process chemistry product and requirements for lowering the overall operating cell voltage. For example, using HBr as the anolyte, with the formation of bromine at the anode, which require a significantly lower anode voltage potential than chlorine formation. Hydroiodic acid, HI, may form iodine at anode potential voltages even lower than that of bromine.

Catholyte cross sectional area flow rates may range from 2 to 3,000 gpm/ft$^2$ or more (0.0076-11.36 m$^3$/m$^2$). Flow velocities may range from 0.002 to 20 ft/sec (0.0006 to 6.1 m/sec).

Catholyte region of the electrochemical cell 110 may include at least one catalyst. The catalyst may be a homogenous heterocyclic catalyst which may be utilized in the catholyte region to improve the Faradaic yield to formate. Homogenous heterocyclic catalysts may include, for example, one or more of pyridine, tin 2-picoline, 4-hydroxy pyridine, adenine, a heterocyclic amine containing sulfur, a heterocyclic amine containing oxygen, an azole, a benzimidazole, a bipyridine, a furan, an imidazole, an imidazole related species with at least one five-member ring, an indole, a lutidine, methylimidazole, an oxazole, a phenanthroline, a pterin, a pteridine, pyridine, a pyridine related species with at least one six-member ring, a pyrrole, a quinoline, or a thiazole, and mixtures thereof.

Operating electrochemical cell 110 at a higher operating pressure in the catholyte region may allow more dissolved $CO_2$ to dissolve in the aqueous electrolyte. Typically, electrochemical cells may operate at pressures up to about 20 to 30 psig in multi-cell stack designs, although with modifications, they could operate at up to 100 psig. The electrochemical cell 110 anolyte may also be operated in the same pressure range to minimize the pressure differential on the membrane separating the two electrode regions. Special electrochemical designs may be required to operate electrochemical units at higher operating pressures up to about 60 to 100 atmospheres or greater, which may be in the liquid $CO_2$ and supercritical $CO_2$ operating range.

In another embodiment, a portion of the catholyte recycle stream may be separately pressurized using a flow restriction with back pressure or using a pump 390 with $CO_2$ injection such that the pressurized stream may be then injected into the catholyte region of the electrochemical cell 110, and potentially increasing the amount of dissolved $CO_2$ in the aqueous solution to improve the conversion yield.

Catholyte region and anolyte region of electrochemical cell 110 may have operating temperatures that may range from −10 to 95° C., more preferably 5-60° C. The lower temperature may be limited by the electrolytes used and their freezing points. In general, the lower the temperature, the higher the solubility of $CO_2$ in the aqueous solution phase of the electrolyte which may result in obtaining higher conversion and current efficiencies. However, operating electrochemical cell voltages may be higher, such that an optimization may be required to produce the chemicals at the lowest operating cost.

The electrochemical cell 110 and the electrochemical acidification electrolyzer 140 may be zero gap, flow-through electrolyzers with a recirculating catholyte electrolyte with various high surface area cathode materials. For example, flooded co-current packed and trickle bed designs with various high surface area cathode materials may be employed. The stack cell design may be bipolar and/or monopolar.

The anode of the electrochemical cell 110 and the electrochemical acidification electrolyzer 140 may include one or more anode coatings. For example, for acid anolytes and oxidizing water under acid conditions, electrocatalytic coatings may include: precious metal and precious metal oxides such as ruthenium and iridium oxides, as well as platinum and gold and their combinations as metals and oxides on valve metal substrates such as titanium, tantalum, or niobium as typically used in the chlor alkali industry or other electrochemical processes which may be stable as anodes. For other anolytes such as alkaline or hydroxide electrolytes electrocatalytic coatings may include carbon, graphite, cobalt oxides, nickel, stainless steels, and their alloys and combinations which may be stable as anodes under alkaline conditions.

Membrane 330, 406*a*, 406*b* may be cation ion exchange type membranes such as those having a high rejection efficiency to anions. For example perfluorinated sulfonic acid based ion exchange membranes such as DuPont Nafion® brand unreinforced types N117 and N120 series, more preferred PTFE fiber reinforced N324 and N424 types, and similar related membranes manufactured by Japanese companies under the supplier trade names such as Flemion®. Other multi-layer perfluorinated ion exchange membranes used in the chlor alkali industry and having a bilayer construction of a sulfonic acid based membrane layer bonded to a carboxylic acid based membrane layer may be employed to efficiently operate with an anolyte and catholyte above a pH of about 2 or higher. These membranes may have a higher anion rejection efficiency. These may be sold by DuPont under their Nafion® trademark as the N900 series, such as the N90209, N966, N982, and the 2000 series, such as the N2010, N2020, and N2030 and all of their types and subtypes. Hydrocarbon based membranes, which may be made from of various cation ion exchange materials may also be used if the anion rejection may be not as critical, such as those sold by Sybron under their trade name Lonac®, AGC Engineering (Asahi Glass) under their Selemion® trade name, and Tokuyama Soda among others.

Alternative Embodiments

Alternative anolyte solutions may be employed to generate chemical products such as bromine at the anode region of electrochemical cell 110, which may be used to brominate organics as intermediates in making ethanol, ethylene, and other chemicals based on bromine chemistry. The use of sulfur compounds in the anolyte region, such as sodium sulfide or $SO_2$ or the use of organics, and conducting the partial oxidation of organics, such as methanol, etc. are also contemplated.

Various alkali metal hydroxides may be employed at the electrochemical cell 110 and/or a thermal reactor 120, 130. For example, hydroxides of lithium, sodium, potassium, and rubidium, and cesium may be used. Further, alkaline earth metal hydroxides may also be used.

Thermal reactors 120, 130 may perform thermal intermolecular condensation reactions using alkali metal hydroxides. Such condensation reactions may include chemical reactions in which two molecules or moieties (functional groups) combine to form one single molecule, together with the loss of a small molecule. When two separate molecules may be reacted, the condensation may be termed intermolecular. Since the reaction occurs at elevated temperatures, the reactions may be characterized as "thermal intermolecular condensation step". If water is lost, the reactions may be characterized as "thermal intermolecular dehydration step". These reactions may occur in an aqueous solution phase, such as with the reaction of CO with the alkali metal hydroxide, or as a melt of the alkali metal carboxylic acid and the alkali metal hydroxide in the thermal reaction.

Thermal reactors 120, 130 may operate at about 40 to 500° C., and more preferably at about 50-450° C. The operating temperatures may depend on the decomposition temperatures of the carboxylic acid and the optimum temperature to get the highest yields of the carboxylic product. A residence time of the reaction at optimum reaction temperatures may range from 5 seconds to hours, and the equipment chosen to conduct the reaction may be designed to provide the rate of heating and cooling required to obtain optimal conversion yields. This may include the use of cold rotating metal that may rapidly chill the hot thermal product after the thermal reaction period is completed.

Thermal reactors 120, 130 may operate in air or an enriched oxygen atmospheres, as well as inert gas atmospheres, such as nitrogen, argon, and helium. Carbon dioxide and hydrogen atmospheres may also be employed to obtain the highest yield in the reaction, as well as partial CO atmospheres. Thermal reactors 120, 130 may be operated under a full or partial vacuum.

The use of CO from other sources, such as from the production of syngas from methane or natural gas reforming may be employed. CO may also come from other sources, such as process waste streams, where may be it separated from carbon dioxide.

Alkali metal hydroxide concentration ranges may be 2% to 99%, more preferably 5 to 98% by weight. The alkali hydroxide may run in molar excess of the alkali metal carboxylic acid being thermally processed in the initial reaction mix or in a continuous process where they may be mixed together. The anticipated molar ratios of the alkali metal carboxylic acid to alkali metal hydroxide may range from 0.005 to 100, and more preferably 0.01 to 50. It may be preferable to use the least amount of alkali metal hydroxide as possible for the reaction to reduce the consumption of the hydroxide in the process.

The process operating equipment that may be employed for thermal reactors 120, 130 may include various commercially available types. For the CO reaction with alkali metal hydroxide, the equipment that may be used may be batch operation equipment, where gas may be injected into a solution mix of the alkali hydroxide. This may also be done in a continuous manner where there may be a feed input of fresh alkali metal hydroxide into a continuous stirred tank reactor (CSTR) with a CO feed into the solution through a gas diffuser into the solution. Alternatively, counter-current packed towers may be used where CO may be injected into the tower counter-current to the flow of alkali metal hydroxide.

For a sodium oxalate operation, thermal reactors 120, 130 may include equipment such as rotary kilns, and single pass plug flow reactors that may be used if the process required the thermal processing of a mixture of alkali metal formate and alkali hydroxide as a solid or hot melt mix. Preferably, the equipment would be operated in a continuous fashion, providing the required residence time for the reaction to go to completion at the selected temperatures, which may then be followed by a cooling section.

A thermal intermolecular condensation process may also be conducted to produce higher carbon content carboxylic acids as well as converting the carboxylic acids into esters, amides, acid chlorides, and alcohols. In addition, the carboxylic acid products may be converted to the corresponding halide compounds using bromine, chlorine, and iodine.

It is contemplated that the electrochemical co-production of products may include a production of a first product, such as reduction of carbon dioxide to carbon-based products to include one, two, three, and four carbon chemicals, at a cathode side of an electrochemical cell with co-production of a second product, such as an oxidized carbon-based product, at the anode of the electrochemical cell where the anolyte comprises a carbon-based reactant and a recycled reactant. Examples of $CO_2$ reduction products at the cathode include CO, formic acid, formaldehyde, methanol, oxalate, oxalic acid, glyoxylic acid, glycolic acid, glyoxal, glycolaldehyde, ethylene glycol, acetic acid, acetaldehyde, ethanol, lactic acid, propanoic acid, acetone, isopropanol, 1-propanol, 1,2-propylene glycol, 1-butanol, and 2-butanol.

A carbon-based reactant may include an oxidizable carbon compound. Carbon-based reactants may include, for example, methane, ethane, ethylene, benzene, toluene, xylene, ethylbenzene, propane, propene, butane, 1-butene, 2-butene, isobutane, ethyl acetate, propionitrile, methyl propionate, ethyl propionate, other alkanes, substituted alkanes, haloalkanes, alkenes, substituted alkenes, haloalkenes, aromatic, haloaromatic, heteroaromatic, and halo-heteroaromatic compounds.

Figure 5:
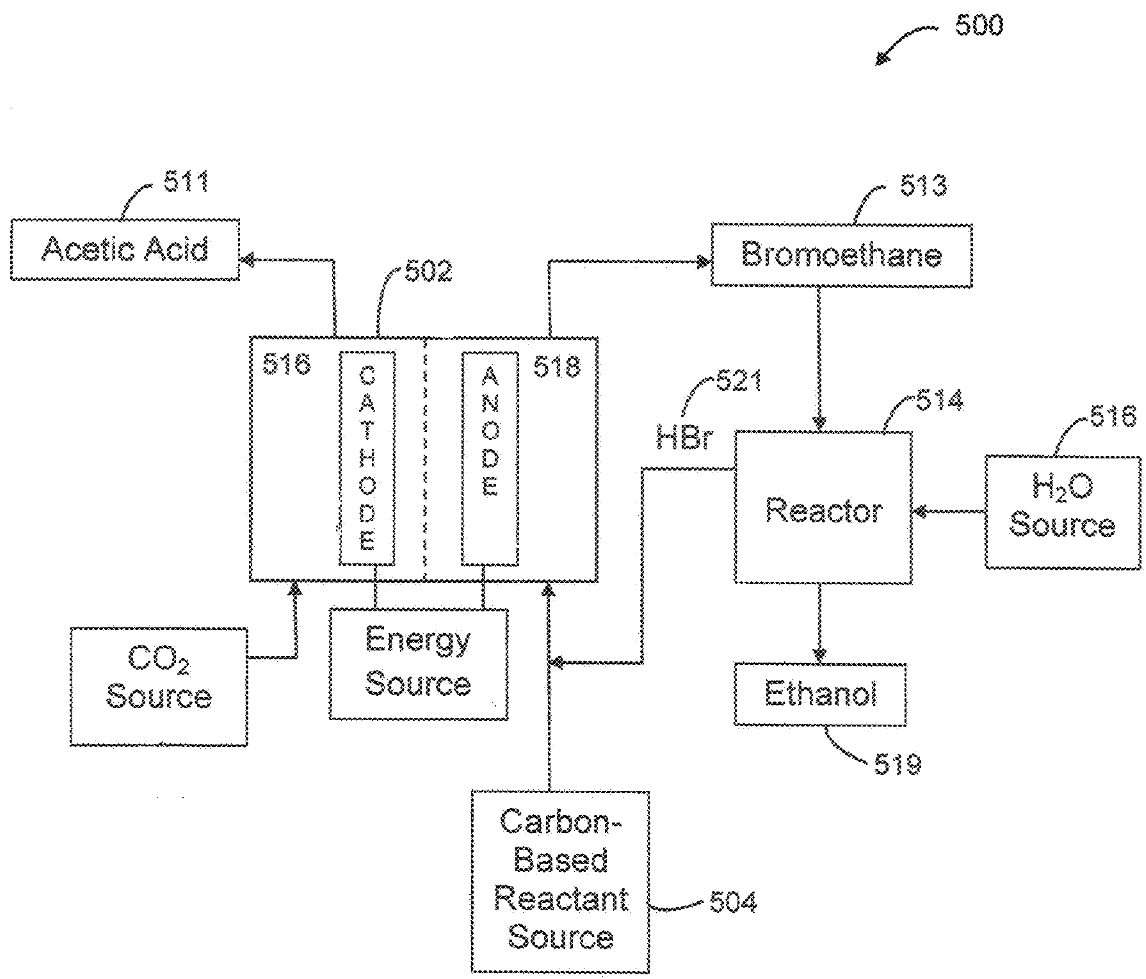
FIGS. 5 and 6 show systems for co-production of products in accordance with an additional embodiment of the present disclosure.
Figure 6:
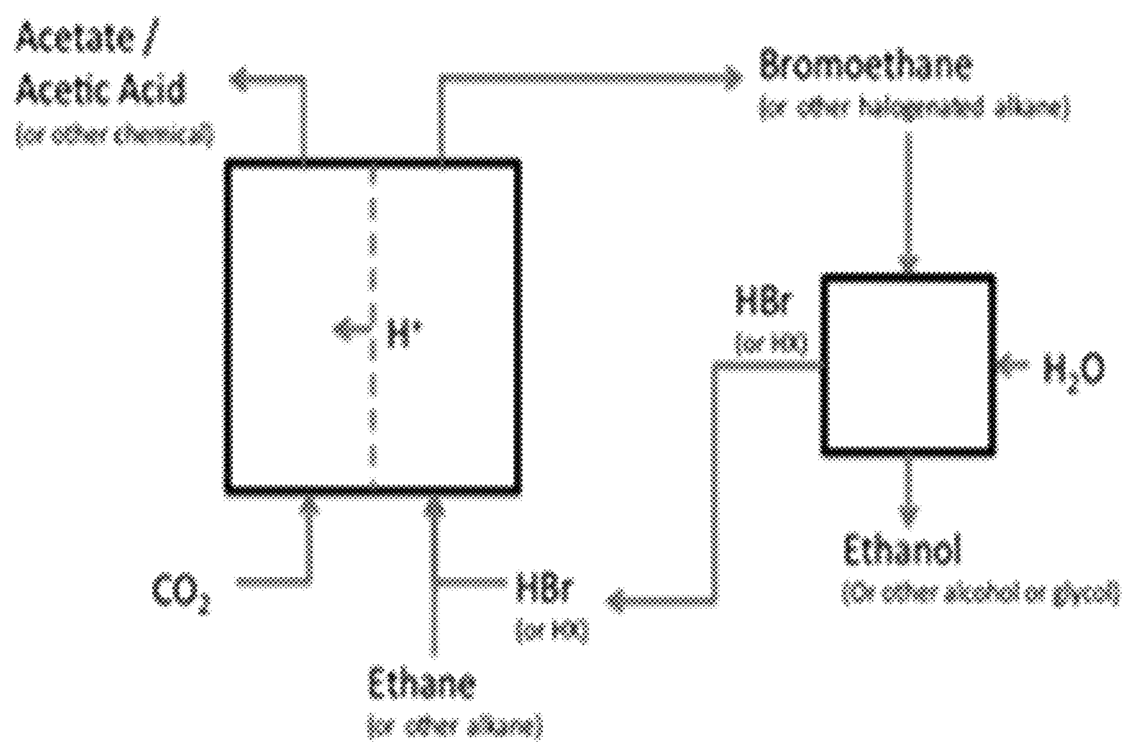

Referring to FIG. 5, a block diagram of a system 500 in accordance with an additional embodiment of the present disclosure is shown. A carbon-based reactant source 504 may supply an alkane, such as ethane and the halogenated compound produced at second region 518 of the electrochemical cell 502 may be bromoethane 513. The carbon-dioxide reduction product may be acetic acid 511. Bromoethane 513 may be supplied to reactor 514 and reacted with water from water source 516 to produce HBr 521 which is recycled as an input feed to the first region 518 and a different compound, such as ethanol 519. In one embodiment of the disclosure, when the carbon dioxide reduction product is acetic acid 511 and ethane is provided by carbon-based reactant source 504, then the molar ratios of the product may be 1 acetic acid:4 ethanol because acetic acid production from $CO_2$ is an 8 electron process and ethanol from ethane is a two electron process. The mass ratios may be 1:3.

It is contemplated that reactions occurring at the first region 516 may occur in a catholyte which may include water, methanol, acetonitrile, propylene carbonate, ionic liquids, or other catholytes. The reactions occurring at the second region 518 may be in a gas phase, for instance in the case of gas phase reactant such as methane or a hydrogen halide. The reaction at the second region 518 may also occur in liquid phase, such as the case of a halide in solution.

In another embodiment, the second region 518 reaction may include an introduction of gas phase benzene into anolyte with gaseous HBr, where HBr is converted to bromine, which reacts with the benzene to produce bromobenzene. A catalyst may be employed to promote the reaction, such as an aluminum or iron-based catalyst, which could be incorporated into the anode structure, especially if it is a high surface area carbon-based material. More preferred, is to generate the bromine in the second region 518 from gaseous HBr, aqueous HBr, or NaBr, and then react the benzene as a liquid or as a gas with the bromine in a reactor containing, for example, an aluminum bromide or iron bromide catalyst on a carbon or inorganic support.

The bromobenzene may then be converted to phenols by a reaction with a sodium hydroxide solution, similar to the hydrolysis of chlorobenzene, with NaOH under pressure. In addition, bromobenzene may be reacted with nitric acid to form p-nitro-bromobenzene, which can then be converted after several other chemical processing steps to p-methoxyphenol. Other chemicals may be produced using bromobenzene as a raw starting material.

It is contemplated that method for production of dicarboxylic acid, such as oxalic acid, may include various steps performed by systems 100, 105, 200 and 205. It may be believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described may be merely explanatory.

What is claimed:

1. A system for producing an oxalic acid comprising:

an electrochemical cell having an anolyte region including an anode and a catholyte region including a cathode separated by at least one ion exchange membrane;

an anolyte feed input operably coupled to the anolyte region of the electrochemical cell, the anolyte feed input includes a hydrogen halide and at least one of a alkane, haloalkane, alkene, haloalkene, aromatic compound, haloaromatic compound, heteroaromatic compound or halo-heteroaromatic compound;

a catholyte feed input operably coupled to the catholyte region of the electrochemical cell, the catholyte feed input includes carbon dioxide and alkali metal hydroxide;

at least one thermal reactor configured to receive a reduction product, generated via a reduction reaction at the catholyte region of the electrochemical cell, and the alkali metal hydroxide;

an electrochemical acidification electrolyzer configured to receive alkali metal oxalate product generated at the at least one thermal reactor and generate oxalic acid, an alkali metal hydroxide and a halogen as an anolyte product; and a source of electrical potential operably connected to the electrochemical cell and the electrochemical acidification electrolyzer, wherein a product is generated via a reaction at the anolyte region of the electrochemical cell.

2. The system of claim 1, wherein the hydrogen halide includes hydrogen bromide.

3. The system of claim 1, wherein the alkali metal hydroxide includes potassium hydroxide.

4. The system of claim 1, wherein the at least one reduction product includes carbon monoxide.

5. The system of claim 1, wherein the at least one thermal reactor configured to receive a reduction product, generated via a reduction reaction at the catholyte region of the electrochemical cell, and the alkali metal hydroxide comprises:

a first thermal reactor configured to receive a carbon monoxide reduction product and the alkali metal hydroxide and generate an alkali metal formate product; and a second thermal reactor configured to receive the alkali metal formate product and an alkali metal hydroxide and generate an alkali metal oxalate product.

6. The system of claim 5, wherein the alkali metal formate product includes potassium formate.

7. The system of claim 1, wherein the electrochemical acidification electrolyzer configured to receive an alkali metal oxalate product comprises:

an electrochemical acidification electrolyzer configured to receive an alkali metal oxalate product at an ion exchange region of the electrochemical acidification electrolyzer at least partially bounded by one or more cation ion exchange membranes.

8. The system of claim 1, wherein the electrochemical acidification electrolyzer includes three compartments.

9. The system of claim 8, wherein the electrochemical acidification electrolyzer includes at least two cation exchange membranes.

10. The system of claim 1, further comprising recycling the alkali metal hydroxide co-generated at the electrochemical acidification electrolyzer to the catholyte feed input.

11. The system of claim 10, further comprising recycling the alkali metal hydroxide co-generated at the electrochemical acidification electrolyzer to the at least one thermal reactor.

12. The system of claim 1, wherein the product generated via a reaction at the anolyte region of the electrochemical cell is a halogenated compound.

13. The method of claim 12, further comprising a reactor configured to receive the halogenated compound and generate a different compound.

* * * * *